US011964250B2

(12) United States Patent
Oh et al.

(10) Patent No.: US 11,964,250 B2
(45) Date of Patent: Apr. 23, 2024

(54) MULTICOMPARTMENT CAPSULES AND METHODS AND SYSTEMS FOR FORMING SAME

(71) Applicant: University of Maryland, College Park, College Park, MD (US)

(72) Inventors: Hyuntaek Oh, College Park, MD (US); Srinivasa R. Raghavan, Columbia, MD (US); William E. Bentley, Annapolis, MD (US); Xi Lu, Abingdon, MD (US); Jessica Lynn Terrell, Philadelphia, PA (US); So Hyun Ahn, College Park, MD (US)

( * ) Notice: Subject to any disclaimer, the term of this patent is extended or adjusted under 35 U.S.C. 154(b) by 1062 days.

(21) Appl. No.: 16/639,152

(22) PCT Filed: Aug. 14, 2018

(86) PCT No.: PCT/US2018/046639
§ 371 (c)(1),
(2) Date: Feb. 14, 2020

(87) PCT Pub. No.: WO2019/036435
PCT Pub. Date: Feb. 21, 2019

(65) Prior Publication Data
US 2020/0171456 A1 Jun. 4, 2020

Related U.S. Application Data

(60) Provisional application No. 62/545,683, filed on Aug. 15, 2017.

(51) Int. Cl.
| | |
|---|---|
| *B01J 13/22* | (2006.01) |
| *B01J 13/10* | (2006.01) |
| *C12M 1/00* | (2006.01) |
| *C12M 1/12* | (2006.01) |
| *A61K 35/12* | (2015.01) |

(52) U.S. Cl.
CPC ............ *B01J 13/22* (2013.01); *B01J 13/10* (2013.01); *C12M 23/34* (2013.01); *C12M 25/16* (2013.01); *A61K 2035/128* (2013.01)

(58) Field of Classification Search
CPC .......... B01J 13/22; B01J 13/10; C12M 23/34; C12M 25/16; A61K 2035/128; A61K 9/5036; A61K 9/5089; A61K 9/5094
USPC ........................................................ 264/4.32
See application file for complete search history.

(56) References Cited

U.S. PATENT DOCUMENTS

| 8,137,728 B2 | 7/2012 | McClements et al. |
| 8,753,655 B2 | 6/2014 | Gunes et al. |
| 2002/0094569 A1* | 7/2002 | Yu .................. C12N 5/0062 435/325 |
| 2003/0194428 A1 | 10/2003 | Miller et al. |
| 2016/0311992 A1 | 10/2016 | Kuczynski et al. |

OTHER PUBLICATIONS

Bertrand et al., Macromol. Rapid Commun. 21(7): 319-348 (2000).*
Ahmed, E.M. (2015) "*Hydrogel: Preparation, Characterization and Applications: A Review,*" J. Advanced Res. 6:105-121.
Bartkowiak, A. et al. (1999) "*Alginate-Oligochitosan Microcapsules: A Mechanistic Study Relating Membrane and Capsule Properties to Reaction Conditions,*" Chem. Mater. 11:2486-2492.
Bertrand, P. et al. (2000) "*Ultrathin Polymer Coatings by Complexation of Polyelectrolytes at Interfaces: Suitable Materials, Structure and Properties,*" Macromolecular Rapid Communications 21(7):319-348.
Buddingh, B.C. et al. (2017) "*Artificial Cells: Synthetic Compartments With Life-Like Functionality and Adaptivity,*" Acc. Chem. Res. 50:769-777.
Chandrawati, R et al. (2011) "*Multicompartment Particle Assemblies for Bioinspired Encapsulated Reactions,*" J. Phys. Chem. Lett. 2:2639-2649.
Chandrawati, R. et al. (2012) "*Biomimetic Liposome- and Polymersome-Based Multicompartmentalized Assemblies,*" Langmuir 28:13798-13807.
De Hoog, H.P.M et al. (2012) "*Self-Assembled Architectures With Multiple Aqueous Compartments,*" Soft Matter 8:4552-4561.
Delcea, M. et al. (2010) "*Multicompartmental Micro- and Nanocapsules: Hierarchy and Applications in Biosciences,*" Macromol. Biosci. 10:465-474.
Deng, N.N. et al. (2016) "*Monodisperse Uni- and Multicompartment Liposomes,*" J. Am. Chem. Soc. 138:7584-7591.
Deng, N.N. et al. (2017) "*Microfluidic Assembly of Monodisperse Vesosomes as Artificial Cell Models,*" J. Am. Chem. Soc. 139:587-590.
Dowling, M.B. et al. (2013) "*Self-Destructing "Mothership" Capsules for Timed Release of Encapsulated Contents,*" Langmuir 29:7993-7998.
Fu, Z.K. et al. (2011) "*Multicompartmentalized Polymersomes for Selective Encapsulation of Biomacromolecules,*" Chem. Commun. 47:2862-2864.
Ghaffarian, R. et al. "*Chitosan-Alginate Microcapsules Provide Gastric Protection and Intestinal Release of ICAM-1-Targeting Nanocarriers, Enabling GI Targeting in Vivo,*" Adv. Funct. Mater., 2016, 26, 3382-3393.

(Continued)

*Primary Examiner* — Hannah J Pak
(74) *Attorney, Agent, or Firm* — HYLTON-RODIC LAW PLLC

(57) ABSTRACT

Methods and systems for synthesizing multicompartment capsules are disclosed, as well as multicompartment polymer capsules formed in accordance with disclosed techniques. At least one plurality of polymer capsules are formed via a capsule-forming process. A feed solution and a reservoir solution are provided, each comprising a biopolymer. The feed solution biopolymer and the reservoir solution biopolymer have opposite charges. Droplets of the feed solution are introduced into the reservoir solution, thereby forming via electrostatic complexation a plurality of polymer capsules. At least a portion of the resulting polymer capsules are then encapsulated in a larger polymer capsule via a similar process, wherein the feed solution utilized for the encapsulation process also comprises the formed smaller capsules.

11 Claims, 12 Drawing Sheets

(56) References Cited

OTHER PUBLICATIONS

Gupta, A. et al. "Encapsulated Fusion Protein Confers "Sense and Respond" Activity to Chitosan-Alginate Capsules to Manipulate Bacterial Quorum Sensing," Biotechnol. Bioeng., 2013, 110, 552-562.
Hosta-Rigau, L. et al. (2011) "Capsosomes With "Free-Floating" Liposomal Subcompartments," Adv. Mater. 23:4082-4085.
Hosta-Rigau, L. et al. (2013) "Advanced Subcompartmentalized Microreactors: Polymer Hydrogel Carriers Encapsulating Polymer Capsules and Liposomes," Small 9:3573-3583.
Jiang, K.Q. et al. (2015) "Microfluidic Generation of Uniform Water Droplets Using Gas as the Continuous Phase," J. Colloid Interface Sci. 448:275-279.
Keating, C.D. (2012) "Aqueous Phase Separation as a Possible Route to Compartmentalization of Biological Molecules," Acc. Chem. Res. 45:2114-2124.
Kim, B.J. et al. (2014) "Cytoprotective Alginate/Polydopamine Core/Shell Microcapsules in Microbial Encapsulation," Angew. Chem., Int. Ed. 53:14443-14446.
Kisak, E.T et al. (2002) "Nanocompartments Enclosing Vesicles, Colloids, and Macromolecules via Interdigitated Lipid Bilayers," Langmuir 18:284-288.
Kisak, E.T. et al. (2004) "The Vesosome—A Multicompartment Drug Delivery Vehicle," Curr. Med. Chem. 11:199-219.
Kontturi, L.S. et al. (2011) "A Laboratory-Scale Device for the Straightforward Production of Uniform, Small Sized Cell Microcapsules With Long-Term Cell Viability," J. Controlled Release 152:376-381.
Kreft, O. et al. (2007) "Remote Control of Bioreactions in Multicompartment Capsules," Adv. Mater., 2007, 19, 3142-3145.
Lee, H.Y. et al. (2011) "Biopolymer Capsules Bearing Polydiacetylenic Vesicles as Colorimetric Sensors of pH and Temperature," Soft Matter 7:3273-3276.
Lee, K.Y. et al. (2012) "Alginate: Properties and Biomedical Applications," Prog. Polym. Sci. 37:106-126.
Lee, M.W. et al. (2012) "A Study of Ejection Modes for Pulsed-DC Electrohydrodynamic Inkjet Printing," J. Aerosol Sci. 46:1-6.
Lentini, R. et al. (2014) "Integrating Artificial With Natural Cells to Translate Chemical Messages That Direct E. coli Behaviour," Nat. Commun. 5:4012:1-6.
Liu, X.M. et al. (2016) "Hierarchical Proteinosomes for Programmed Release of Multiple Components," Angew. Chem., Int. Ed. 55:7095-7100.
Marguet, M. et al. (2013) "Multicompartmentalized Polymeric Systems: Towards Biomimetic Cellular Structure and Function," Chem. Soc. Rev. 42:512-529.
Ohkawa, K. et al. (2004) "Preparation and Characterization of Chitosan-Gellan Hybrid Capsules Formed by Self-Assembly at an Aqueous Solution Interface," Macromol. Mater. Eng. 289:33-40.
Payne, G. F. et al. (2013) "Accessing Biology's Toolbox for the Mesoscale Biofabrication of Soft Matter," Soft Matter 9:6019-6032.
Peniche, C. et al. (2003) "Chitosan: An Attractive Biocompatible Polymer for Microencapsulation," Macromol. Biosci. 3:511-520.
Pereira, C.S. et al. (2013) "AI-2-Mediated Signalling in Bacteria," FEMS Microbiol. Rev. 37:156-181.
Perro, A. et al. (2011) "Mastering a Double Emulsion in a Simple Co-Flow Microfluidic to Generate Complex Polymersomes," Langmuir 27:9034-9042.
Peters, R. et al. (2014) "Cascade Reactions in Multicompartmentalized Polymersomes," Angew. Chem., Int. Ed. 53:146-150.
Seemann, R. et al. (2012) "Droplet Based Microfluidics," Rep. Prog. Phys., 2012, 75, 016601.
Shah, R.K. et al. "Designer Emulsions Using Microfluidics," Mater. Today 11:18-27.
Shum, H.C. et al. (2011) "Multicompartment Polymersome Gel for Encapsulation," Soft Matter, 2011, 7,8762-8765.
Siti, W. et al. (2014) "An Intercompartmental Enzymatic Cascade Reaction in Channel-Equipped Polymersome-in-Polymersome Architectures," J. Mater. Chem. B, 2014, 2, 2733-2737.
Stadler, B. et al. (2009) "Polymer Hydrogel Capsules: En Route Toward Synthetic Cellular Systems," Nanoscale, 2009, 1, 68-73.
Tsao, C.Y. et al. (2010) "Autonomous Induction of Recombinant Proteins by Minimally Rewiring Native Quorum Sensing Regulon of E. coli," Metab. Eng. 12:291-297.
Van Dongen, S.F.M. et al. (2009) "Three-Enzyme Cascade Reaction Through Positional Assembly of Enzymes in a Polymersome Nanoreactor," Chem. Eur. J. 15:1107-1114.
Walker, S.A. et al. (1997) "Encapsulation of Bilayer Vesicles by Self-Assembly," Nature 387:61-64.
Wang, L. et al. (2005) "LuxS-Dependent Gene Regulation in Escherichia coli K-12 Revealed by Genomic Expression Profiling," J. Bacteriol. 187:8350-8360.
Weitz, M. et al. (2014) "Communication and Computation by Bacteria Compartmentalized Within Microemulsion Droplets," J. Am. Chem. Soc. 136:72-75.
Williams, P. (2007) "Quorum Sensing, Communication and Cross-Kingdom Signalling in the Bacterial World," Microbiology 153:3923-3938.
Wu, H.C. et al. (2013) "Autonomous Bacterial Localization and Gene Expression Based on Nearby Cell Receptor Density," Mol. Syst. Biol., 2013, 9, 636.
Zargar, A. et al. (2017) "Constructing 'Quantized Quorums' to Guide Emergent Phenotypes Through Quorum Quenching Capsules," Biotechnol. Bioeng. 114:407-415.

* cited by examiner (a) Effect of flow rate, frequency on capsule size (b) Images of capsules at different flow rates and frequencies (a) MCCs with Distinct Inner Compartments Containing Two Types of Fluorescent Particles (b) MCCs with Distinct Inner Compartments Containing Two Strains of Fluorescent *E. coli*

(A) MCC has two strains of E. coli in two compartments (B) AI-2 produced in the P compartment diffuses out (C) AI-2 diffuses into the R compartment (D) Reporter E. coli generate fluorescent protein in response (1) 1 Producer, 1 Reporter (2) 2 Producers, 1 Reporter (3) 1 Producer, 2 Reporters

MULTICOMPARTMENT CAPSULES AND METHODS AND SYSTEMS FOR FORMING SAME

CROSS-REFERENCE TO RELATED APPLICATION

This application is a § 371 National Stage Application of PCT/US2018/046639 (filed Aug. 14, 2018), which application is based on U.S. Provisional Patent Application Ser. No. 62/545,683, filed Aug. 15, 2017, entitled *"Method for Synthesizing MulticompartmentCapsules with Distinct Contents in Each Internal Compartment,"* each of which applications is incorporated herein by reference in its entirety and to which priority is claimed.

FIELD OF THE INVENTION

The present invention relates to methods and systems for synthesizing multicompartment polymer capsules, including multicompartment capsules comprising inner compartments having distinct contents therein.

BACKGROUND OF THE INVENTION

Over the past two decades, the search for new materials has increasingly drawn inspiration from biology (Biofabrication: Micro- and Nano-fabrication, Printing, Patterning and Assemblies, ed. G. Forgacs and W. Sun, William Andrew, New York, 2013; Bio-inspired Materials for Biomedical Engineering, ed. A. B. Brennan and C. M. Kirschner, Wiley, New York, 2014). Although numerous advances in biomimetic materials have now been reported, there still remains a large gap between structures that can be designed in the laboratory and those found in biology.

A prototypical example is that of a eukaryotic cell, shown in cross-section in FIG. 1 (Alberts, B. Molecular Biology of the Cell, Garland Publishers, New York, 4th ed., 2002). The cell is a remarkable multifunctional material. It is capable of synthesizing proteins and lipids, storing and harvesting energy, storing and retrieving genetic information, and recycling used or defective material. The ability of the cell to accomplish these diverse tasks is intimately related to its architecture, i.e., to the fact that it has multiple distinct internal compartments (organelles), each bounded by a lipid membrane. Each organelle is surrounded by a distinct membrane and has unique internal contents; consequently, each organelle has a distinct function within the cell. For example, in animal cells, the Golgi bodies serve as centers for protein and lipid synthesis, the mitochondria as the power plants where energy is stored, and the lysosomes as the recycling centers where proteins are degraded (id.). The function of each organelle is tied to its unique internal constituents. At the same time, the membrane around the organelle tightly regulates the entry and exit of molecules. For example, lysosomes maintain a highly acidic pH, which enables hydrolytic degradation of proteins—however, this acid does not pass through into the surrounding cytoplasm.

In recent years, several researchers have attempted to create artificial cells, sometimes referred to as protocells, with compartmentalized architecture such as found in biological cells (Stadler, B. et al. *Polymer Hydrogel Capsules: En Route Toward Synthetic Cellular Systems*, Nanoscale, 2009, 1, 68-73; Delcea, M. et al. *Multicompartmental Micro- and Nanocapsules: Hierarchy and Applications in Biosciences*, Macromol. Biosci., 2010, 10, 465-474; Chandrawati, R et al. *Multicompartment Particle Assemblies for Bioinspired Encapsulated Reactions*, J. Phys. Chem. Lett., 2011, 2, 2639-2649; Chandrawati, R. and Caruso, F. *Biomimetic Liposome- and Polymersome-Based Multicompartmentalized Assemblies*, Langmuir, 2012, 28, 13798-13807; de Hoog, H. P. M et al. *Self-Assembled Architectures with Multiple Aqueous Compartments*, Soft Matter, 2012, 8, 4552-4561; Keating, C. D. *Aqueous Phase Separation as a Possible Route to Compartmentalization of Biological Molecules*, Acc. Chem. Res., 2012, 45, 2114-2124; Marguet, M. et al. *Multicompartmentalized Polymeric Systems: Towards Biomimetic Cellular Structure and Function*, Chem. Soc. Rev., 2013, 42, 512-529; Buddingh, B. C. and van Hest, J. C. M. *Artificial Cells: Synthetic Compartments with Lifelike Functionality and Adaptivity*, Acc. Chem. Res., 2017, 50, 769-777).

Exemplary protocells include polymersome-in-polymersome structures (van Dongen, S. F. M. et al. *Three-Enzyme Cascade Reaction through Positional Assembly of Enzymes in a Polymersome Nanoreactor*, Chem. Eur. J., 2009, 15, 1107-1114; Fu, Z. K. et al. *Multicompartmentalized Polymersomes for Selective Encapsulation of Biomacromolecules*, Chem. Commun., 2011, 47, 2862-2864; Perro, A. et al. *Mastering a Double Emulsion in a Simple Co-Flow Microfluidic to Generate Complex Polymersomes*, Langmuir, 2011, 27, 9034-9042; Shum, H. C. and Weitz, D. A. *Multicompartinent Polymersome Gel for Encapsulation*, Soft Matter, 2011, 7, 8762-8765; Shum, H. C. et al. *Multicompartment Polymersomes from Double Emulsions*, Angew. Chem., Int. Ed., 2011, 50, 1648-1651; Peters, R. et al. *Cascade Reactions in Multicompartmentalized Polymersomes*, Angew. Chem., Int. Ed., 2014, 53, 146-150; Siti, W. et al. *An Intercompartmental Enzymatic Cascade Reaction in Channel-Equipped Polymersome-in-Polymersome Architectures*, J. Mater. Chem. B, 2014, 2, 2733-2737), and liposome-in-liposome structures (Walker, S. A. et al. *Encapsulation of Bilayer Vesicles by Self-Assembly*, Nature, 1997, 387, 61-64; Kisak, E. T et al. *Nanocompartments Enclosing Vesicles*, Colloids, And Macromolecules Via Interdigitated Lipid Bilayers, Langmuir, 2002, 18, 284-288; Kisak, E. T. et al. *The Vesosome —A Multicompartment Drug Delivery Vehicle*, Curr. Med. Chem., 2004, 11, 199-219; Deng, N. N. et al. *Monodisperse Uni- and Multicompartment Liposomes*, J. Am. Chem. Soc., 2016, 138, 7584-7591; Deng, N. N. et al. *Microfluidic Assembly of Monodisperse Vesosomes as Artificial Cell Models*, J. Am. Chem. Soc., 2017, 139, 587-590). Attempts have been made to utilize such structures to run enzymatic cascade reactions (van Dongen, S. F. M. et al. *Three-Enzyme Cascade Reaction through Positional Assembly of Enzymes in a Polymersome Nanoreactor*, Chem.-Eur. J., 2009, 15, 1107-1114; Peters, R. et al. *Cascade Reactions in Multicompartmentalized Polymersomes*, Angew. Chem., Int. Ed., 2014, 53, 146-150; Siti, W. et al. *An Intercompartmental Enzymatic Cascade Reaction in Channel-Equipped Polymersome-in-Polymersome Architectures*, J. Mater. Chem. B, 2014, 2, 2733-2737).

However, there are various drawbacks associated with such prior methods and protocells. In some cases, the compartments lack a membrane (Keating, C. D. *Aqueous Phase Separation as a Possible Route to Compartmentalization of Biological Molecules*, Acc. Chem. Res., 2012, 45, 2114-2124), or have coexisting oil and water phases (Weitz, M. et al. *Communication and Computation by Bacteria Compartmentalized within Microemulsion Droplets*, J. Am. Chem. Soc., 2014, 136, 72-75), or are stable only in non-aqueous solvents (Liu, X. M. et al. *Hierarchical Proteinosomes for Programmed Release of Multiple Components*, Angew. Chem., Int. Ed., 2016, 55, 7095-7100). The oil or solvents are problematic for encapsulation of biological payloads. Moreover, a real, biological cell is not an emulsion in terms of its structure.

Other attempts provide for the synthesis of the individual compartments using a layer-by-layer assembly of polymers around a core template, followed by removal of the template (Hosta-Rigau, L. et al. *Capsosomes with "Free-Floating" Liposomal Subcompartments*, Adv. Mater., 2011, 23, 4082-4085; Hosta-Rigau, L. et al. *Advanced Subcompartmentalized Microreactors: Polymer Hydrogel Carriers Encapsulating Polymer Capsules and Liposomes*, Small, 2013, 9, 3573-3583). Such layer-by-layer assembly is a laborious process, involving 50 or more consecutive process steps. The necessity for a template adds further complexity to the process, given conditions for subsequent removal of the template require harsh agents (e.g., dissolution of silica using acids). Moreover, when the template is removed, one obtains a core that does not contain any payload. As such, strategies must then be devised for loading the empty core with appropriate contents.

Thus, prior methods for synthesizing multicompartment protocells are extremely complex and expensive. In addition, it is difficult to control the number of individual compartments as well as their specific contents using such methods. Moreover, polymersomes require block copolymers that typically need to be synthesized and are not commercially available. Thus, while prior attempts have achieved some success, a simple and versatile method to create multicompartment protocells is still lacking. Accordingly, it would be beneficial to provide a method of synthesizing multicompartment capsules, and the resulting multicompartment capsules, that overcome some or all of the disadvantages associated with prior methods and structures.

SUMMARY OF THE INVENTION:

The present invention is directed to methods of synthesizing biopolymer microcapsules, and microcapsules formed in accordance with such methods, having a compartmentalized architecture similar to that found in biological (e.g., eukaryotic) cells. To synthesize these capsules, a biocompatible method is provided that utilizes aqueous media, and thus avoids the use of oil phases, requires no sacrificial templates, and employs a minimal number of process steps. The disclosed techniques exploit the electrostatic complexation of oppositely charged polymers dissolved in aqueous media. In accordance with disclosed embodiments, droplets of an anionic biopolymer are generated using a simple microcapillary device, with the droplets being sheared off the capillary tip by pulses of gas (air or nitrogen). The liquid droplets are then introduced into a reservoir whereupon they encounter multivalent cations as well as a cationic biopolymer. A solid shell is thereby formed around each droplet by electrostatic interactions between the polymers while the core is ionically cross-linked into a gel. Next, a discrete number of these capsules are encapsulated within a larger outer capsule by repeating the same process with a wider capillary.

The disclosed techniques allow for precise control of the overall diameter of the multicompartment capsules (MCCs), e.g., between about 100 μm and about 1 mm, or between about 300 and about 500 μm. The diameters of each of the inner compartments may be precisely controlled, e.g. between about 50 μm and about 500 μm, or between about 100 μm and about 300 μm. In addition, the total number of inner compartments in an MCC may be precisely controlled, e.g. 1, 2, 3, 4, 5, 6, 7, 8, 9, 10, 15, 20, 25 or more inner compartments. Further, the same or different payloads may be encapsulated in each of the inner compartments, including colloidal particles, enzymes, microbial cells, and/or other therapeutic agents, in all cases preserving their native functions and/or chemistries.

A hallmark of biological cells is the existence of cascade processes, where products created in one organelle are transported and used in another. As a demonstration of the capabilities exhibited by the disclosed MCCs of the present invention, a cascade process was studied involving two strains of bacteria (*E. coli*), which communicate through small molecules known as autoinducers. In one compartment of the MCC, *E. coli* that produces autoinducer 2 (AI-2) in the presence of growth media was cultivated. As demonstrated, the AI-2 then diffused into an adjacent compartment within the MCC, wherein a reporter strain of *E. coli* was cultivated. The reporter *E. coli* imbibed the AI-2 and in turn, produced a fluorescence response. Thus, the action (AI-2 production) and response (fluorescence signal) were localized within different compartments in the same MCC.

Thus, the MCCs produced in accordance with disclosed embodiments exhibit structure and functionality similar to that of biological cells. For example, an artificial cell structure is shown in FIG. 2, which includes features corresponding to those of the exemplary cell shown in FIG. 1. The artificial cell includes a large container or capsule with several smaller internal compartments. Thus, in order to create such a structure, methods of synthesis provide for the control of compartment number, size and contents. For example, as shown in FIG. 2, a total of 15 inner compartments are provided: a large compartment (designated as "A") with certain contents; 4 smaller compartments (each designed as "B") with another set of contents; and 10 much smaller compartments (each designated as "C") with a third set of contents. All compartments may have an aqueous interior with a composition (pH and ionic strength) compatible with biological media. In this way, payloads such as biomolecules (e.g., proteins, nucleic acids) and/or live cells (e.g., microorganisms, mammalian, plant cells) may be encapsulated in these compartments. In accordance with disclosed techniques, such MCCs may be synthesized using relatively inexpensive materials, and via simple, quick, and straightforward process steps.

In some embodiments, the present invention relates to a method of synthesizing a multicompartment capsule. At least one plurality of polymer capsules if formed via a capsule-forming process, wherein the capsule-forming process comprises: providing a feed solution comprising a biopolymer; providing a reservoir solution comprising a biopolymer, wherein the feed solution biopolymer and the reservoir solution biopolymer have opposite charges; introducing droplets of the feed solution into the reservoir solution, thereby forming via electrostatic complexation a plurality of polymer capsules. At least one of the polymer capsule(s) formed from the prior capsule-forming process is then encapsulated in an outer polymer shell. The encapsulation process comprises: providing a feed solution comprising a biopolymer and at least one polymer capsule(s) from the formed plurality of polymer capsules; providing a reservoir solution comprising a biopolymer, wherein the feed solution biopolymer and the reservoir solution biopolymer have opposite charges; introducing droplets of the feed solution into the reservoir solution, thereby forming via electrostatic complexation a plurality of outer polymer shells. At least one of the outer polymer shells encapsulates the at least one polymer capsule(s), thereby forming a multicompartment capsule.

In some embodiments, the feed solution further comprises a payload, wherein at least one polymer capsule(s) from the formed polymer capsules encapsulates the payload.

In some embodiments, the capsule-forming process is repeated, thereby forming one or more additional pluralities of polymer capsules. In some implementations, at least one polymer capsule from each formed plurality of polymer capsules is encapsulated in the outer polymer shell.

In some embodiments, the resulting multicompartment capsule encapsulates two or more polymer capsules having different diameters. In some embodiments, the multicompartment capsule encapsulates two or more polymer capsules having different payloads.

In some embodiments, the feed solution comprises one of an anionic biopolymer or a cationic biopolymer, and the reservoir solution comprises the other of the anionic biopolymer or the cationic biopolymer. Various biopolymers are suitable for use with the disclosed methods, as would be readily appreciated by one of ordinary skill in the art (e.g., collagen, gelatin, dextran, chitosan, cellulose, alginate, starch, agarose, etc.) (see, e.g., Payne, G. F. et al. *Accessing biology's toolbox for the mesoscale biofabrication of soft matter*, Soft Matter 9, 6019-6032 (2013); see also Ahmed, E. M. *Hydrogel: Preparation, characterization and applications: A review*, J. Advanced Res., 6, 105-121 (2015)).

In some embodiments, the method of synthesizing the multicompartment capsule includes the further steps of: channeling the feed solution through a first capillary; and exposing a tip of the first capillary to pulses of gas and thereby dislodging via each pulse of gas a droplet of the feed solution from the tip, wherein the dislodged droplets of the feed solution are introduced into the reservoir solution. In some implementations, the method comprises the additional step of selecting a size of the dislodged droplets by: adjusting a flow rate of the feed solution through the first capillary, and/or adjusting pulsing frequency of gas.

In some embodiments, the method comprises channeling the feed solution through a second capillary, and exposing a tip of the second capillary to pulses of gas, thereby dislodging via each pulse of gas a droplet of the feed solution from the tip. The dislodged droplets of the feed solution are thereby introduced into the reservoir solution. In some implementations, the method further comprises selecting a size of the dislodged droplets by adjusting a flow rate of the feed solution through the second capillary, and/or adjusting pulsing frequency of gas. In some embodiments, the first capillary has a first diameter, and the second capillary has a second diameter greater than the first diameter.

In some embodiments, at least one of the encapsulated polymer capsule(s) has a diameter of between about 50 μm and about 500 μm, or between about 100 μm and about 300 μm. In some embodiments, the multicompartment capsule has a diameter of between about 100 μm and about 1 mm, or between about 300 and about 500 μm.

In some embodiments, the multicompartment capsule encapsulates two or more polymer capsules, wherein one of the polymer capsules encapsulates a first payload and another of the polymer capsules encapsulates a second payload. The first payload and/or the second payload may be selected from a wide variety of agents, e.g., including a biological cell (including, e.g., bacteria, archaea, eukaryota), a biomolecule (including, e.g., enzyme, protein, carbohydrate, lipid, nucleic acid), a therapeutic agent, and a detectable or diagnostic agent (fluorescent, magnetic). Therapeutic agents may include, e.g., antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding (minor groove) compounds, hormones, vitamins, proteins, peptides, polypeptides and peptide-like therapeutic agents. Diagnostic or detectable agents include, e.g., dyes, contrast agents, fluorescent agents, radioisotopes, magnetic particles, etc.

In some embodiments, at least one encapsulated capsule(s) has an outer membrane permeable to ions and small molecules (e.g., molecules having a molecular weight of less than about 900 Da and/or a diameter of less than about 1 nm). In some embodiments, at least one encapsulated capsule(s) has an outer membrane impermeable to molecules having a diameter greater than about 1 nm.

The present invention also relates to a system for synthesizing a multicompartment capsule, comprising: a pump configuring to retain a feed solution and control flow rate of the feed solution, wherein the feed solution comprises: a biopolymer; a capillary in fluid communication with the feed solution from the pump; a sheath surrounding the capillary; a flow regulator in fluid communication with a gas source and the sheath and configured to control gas flow and pressure therebetween; and a collection reservoir configured to retain a reservoir solution, wherein the reservoir solution comprises a biopolymer. Droplets of the feed solution released from the capillary are introduced into the reservoir solution and form capsules therein via electrostatic complexion.

In some embodiments, the system comprises a function generator in communication with the gas flow regulator and configured to control pulsing frequency of the gas flow to the sheath. In some embodiments, the feed solution biopolymer and the reservoir solution biopolymer have opposite charges. In some embodiments, the feed solution further comprises a payload, wherein at least a portion of the formed capsules encapsulate the payload when the feed solution is introduced into the reservoir solution. A wide variety of payloads may be provided, including, e.g., a biological cell (e.g., bacteria, archaea, eukaryota), a biomolecule (e.g., enzyme, protein, carbohydrate, lipid, nucleic acid), a therapeutic agent, and/or a detectable agent.

In some embodiments, the capillary of the system is a first capillary configured to release droplets having a first diameter. The system may additionally comprise at least a second capillary configured to release droplets having a second diameter greater than the first diameter.

The present invention also relates to multicompartment capsule(s) formed by any of the disclosed methods herein. In some embodiments, a multicompartment polymer capsule comprises one or more inner capsule(s) each having a membrane encapsulating an aqueous core, and an outer polymer shell encapsulating the inner capsule(s).

In some embodiments, the capsule comprises a membrane permeable to ions and small molecules (e.g. molecules having a molecular weight of less than about 900 Da and/or a diameter of less than about 1 nm). In some embodiments, the membrane is impermeable to molecules having a diameter greater than about 1 nm.

In some embodiments, the multicompartment polymer capsule comprises at least two of the inner capsules. In some implementations, one of the inner capsules has a first diameter and another of the inner capsules has a second diameter different than the first diameter. In some embodiments, the inner core of one of the inner capsules comprises a first payload and the inner core of another of the inner capsules comprises a second payload. The payloads may be the same or different. The payloads may be selected from a wide variety of molecules and/or substances, including, e.g., a biological cell (e.g., bacteria, archaea, eukaryota), a biomolecule (e.g., enzyme, protein, carbohydrate, lipid, nucleic acid), a therapeutic agent, and/or a detectable agent. In some embodiments, one of the inner capsules comprises a first biopolymer composition, and another of the inner capsules comprises a second biopolymer composition different than the first biopolymer composition. In some embodiments, the inner core(s) comprises an aqueous interior having a composition compatible with biological media.

DETAILED DESCRIPTION OF EMBODIMENTS OF THE INVENTION

Figure 1:
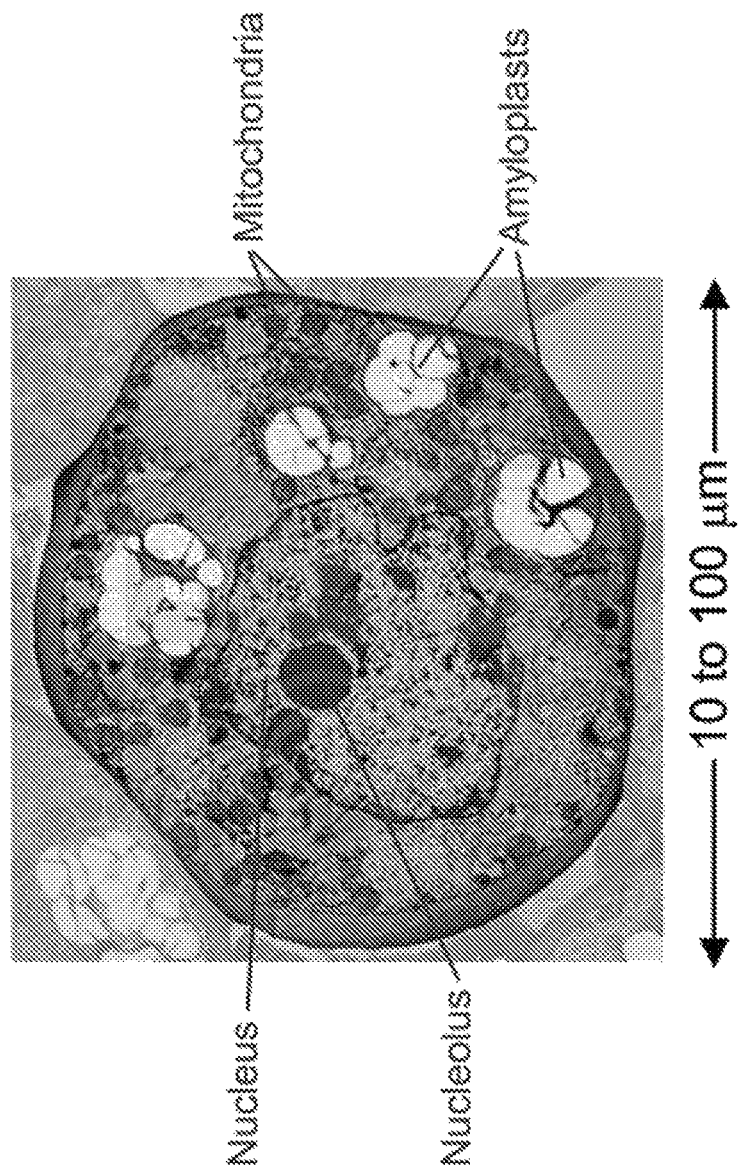
FIG. 1 illustrates the architecture of an exemplary eukaryotic cell. A cross-section of a parenchymal cell from a lily plant is shown with different organelles indicated.
Figure 2:
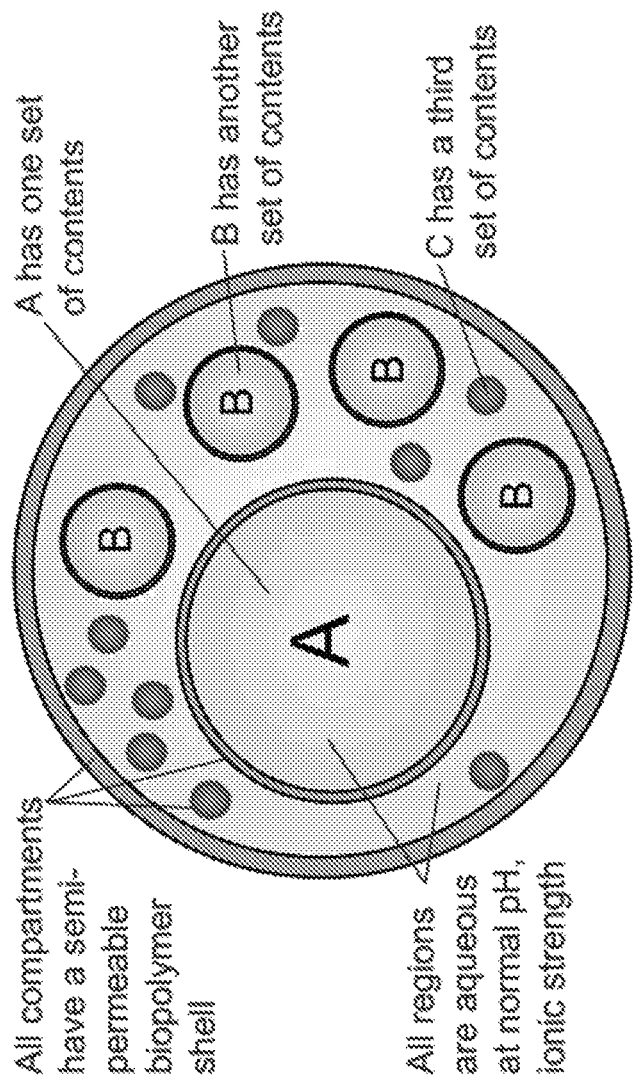
FIG. 2 illustrates schematically the architecture of a cell-mimicking microcapsule. The biopolymer-based microcapsule mimics the structure of the exemplary cell shown in FIG. 1. Three different types of internal compartments (A, B, C) are shown, with each component type having a similar size and similar contents. The multicompartment capsule (MCC) of the present invention is based on water at physiological pH and ionic strength.

The present invention is directed to methods of synthesizing an artificial cell structure or micro capsule. The term "capsule" refers to a structure having an inner aqueous core surrounded by a polymeric outer membrane or shell. The outer shell may be permeable to small molecules and ions, but not to macromolecules or nanoparticles (see, e.g., Stadler, B. et al. *Polymer Hydrogel Capsules: En Route Toward Synthetic Cellular Systems*, Nanoscale, 2009, 1, 68-73). The overall structure is referred to herein as a "multicompartment capsule" (MCC). For example, an MCC having an outer shell and multiple smaller interior compartments is shown in FIG. 2.

In accordance with disclosed embodiments, MCCs are synthesized by electrostatic complexation (see, e.g., Bartkowiak, A. and Hunkeler, D. *Alginate-Oligochitosan Microcapsules: A Mechanistic Study Relating Membrane and Capsule Properties to Reaction Conditions*, Chem. Mater., 1999, 11, 2486-2492; Ohkawa, K. et al. *Preparation and Characterization of Chitosan- Gellan Hybrid Capsules Formed by Self-Assembly at an Aqueous Solution Interface*, Macromol. Mater. Eng., 2004, 289, 33-40; Lee, H. Y. et al. *Biopolymer Capsules Bearing Polydiacetylenic Vesicles as Colorimetric Sensors of pH and Temperature*, Soft Matter, 2011, 7, 3273-3276; Dowling, M. B. et al. *Self-Destructing "Mothership" Capsules for Timed Release of Encapsulated Contents*, Langmuir, 2013, 29, 7993-7998; Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562; Ghaffarian, R. et al. Chitosan-Alginate *Microcapsules Provide Gastric Protection and Intestinal Release of ICAM-*1*-Targeting Nanocarriers*, Enabling GI Targeting In Vivo, Adv. Funct. Mater., 2016, 26, 3382-3393; Zargar, A. et al. *Constructing 'Quantized Quorums' to Guide Emergent Phenotypes Through Quorum Quenching Capsules*, Biotechnol. Bioeng., 2017, 114, 407-415). Various common biopolymers may be utilized for constructing the MCCs, e.g., such as alginate (Lee, K. Y. and Mooney, D. J. *Alginate: Properties and Biomedical Applications*, Prog. Polym. Sci., 2012, 37, 106-126) and chitosan (Peniche, C. et al. *Chitosan: An Attractive Biocompatible Polymer for Microencapsulation*, Macromol. Biosci., 2003, 3, 511-520), which are widely used in many biomedical studies and applications. However, it should be understood that various other biopolymers may alternatively be used (e.g., collagen, gelatin, dextran, cellulose, starch, agarose, etc.) (see, e.g., Payne, G. F. et al. *Accessing biology's toolbox for the mesoscale biofabrication of soft matter*, Soft Matter 9, 6019-6032 (2013)), and thus the present invention is not so limited.

In some embodiments, biopolymer-bearing aqueous droplets are generated by a relatively simple microfluidic device constructed from glass or plastic tubing and using pulses of gas (e.g., air). The resulting droplets are subsequently converted to capsules by electrostatic complexation. A subsequent microfluidic step is then provided for encapsulating one or more small capsules in a larger capsule. Preferably, no immiscible oil phase is used in any processing steps. As such, intact biological payloads such as proteins and cells may be readily encapsulated in individual compartments of the MCC.

Payloads encapsulated in the capsules may be selected from a wide variety of agents, e.g., including biological cells (including, e.g., bacteria, archaea, eukaryota), biomolecules (including, e.g., enzyme, protein, carbohydrate, lipid, nucleic acid), therapeutic agents, and detectable or diagnostic agents (fluorescent, magnetic). Therapeutic agents may include, e.g., antibiotics, antivirals, antifungals, anti-angiogenics, analgesics, anesthetics, anti-inflammatory agents including steroidal and non-steroidal anti-inflammatories (NSAIDs), corticosteroids, antihistamines, mydriatics, antineoplastics, immunosuppressive agents, anti-allergic agents, metalloproteinase inhibitors, tissue inhibitors of metalloproteinases (TIMPs), vascular endothelial growth factor (VEGF) inhibitors or antagonists or intraceptors, receptor antagonists, RNA aptamers, antibodies, hydroxamic acids and macrocyclic anti-succinate hydroxamate derivatives, nucleic acids, plasmids, siRNAs, vaccines, DNA binding compounds, hormones, vitamins, proteins, peptides, polypeptides and peptide-like therapeutic agents. Diagnostic or detectable agents include, e.g., dyes, contrast agents, fluorescent agents, radioisotopes, magnetic particles, etc.

The disclosed techniques advantageously provide for payload encapsulation and capsule formation in a single step. Thus, the contents of each compartment of the MCC may be precisely controlled. Also, due to the use of relatively inexpensive biopolymers and tubing, the disclosed techniques are readily accessible to any laboratory, and the same platform may be used to construct a variety of cell-like structures. Access to microfabrication facilities or a clean room is not necessary, and the device may be operated by virtually anyone with only minimal training.

As noted above, the cell-like structure of the MCC allows encapsulated payloads to be kept separate in distinct compartments therein, while the proximity of the compartments enables cascade reactions. To demonstrate these features, two strains of genetically engineered *E. coli* were cultivated in adjacent compartments of an MCC. One *E. coli* strain was a producer (P) (see, e.g., Wang, L. et al. *luxSDependent Gene Regulation in Escherichia coli K-12 Revealed by Genomic Expression Profiling*, J. Bacteriol., 2005, 187, 8350-8360; Wu, H. C. et al. *Autonomous Bacterial Localization and Gene Expression Based on Nearby Cell Receptor Density*, Mol. Syst. Biol., 2013, 9, 636; Tsao, C. Y. et al. *Autonomous Induction of Recombinant Proteins by Minimally Rewiring Native Quorum Sensing Regulon of E. coli*, Metab. Eng., 2010, 12, 291-297), which produced a small molecule called autoinducer-2 (AI-2) that is involved in a bacterial signaling process called quorum sensing (QS) (Williams, P. *Quorum Sensing, Communication and Cross-Kingdom Signalling in the Bacterial World*, Microbiology, 2007, 153, 3923-3938; Pereira, C. S. et al. *AI-2-Mediated Signalling in Bacteria*, FEMS Microbiol. Rev., 2013, 37, 156-181). The AI-2 formed in the producer compartment then diffused into adjacent compartment(s) where a second reporter (R) strain of *E. coli* was cultivated. The reporter *E. coli* responded to the AI-2 by turning on a gene that produces a fluorescent protein (Wu, H. C. et al. *Autonomous Bacterial Localization and Gene Expression Based on Nearby Cell Receptor Density*, Mol. Syst. Biol., 2013, 9, 636; Tsao, C. Y. et al. *Autonomous Induction of Recombinant Proteins by Minimally Rewiring Native Quorum Sensing Regulon of E. coli*, Metab. Eng., 2010, 12, 291-297). The response in the reporter compartments was observed visually by fluorescence microscopy.

As demonstrated, the MCCs of the present invention may be used to study a cascade process involving two microorganisms in close proximity within the same environment. The MCCs may be used to juxtapose a wide variety of microorganisms, including those that could not be cultured together using prior techniques, and to evaluate cross-kingdom communication (Williams, P. *Quorum Sensing, Communication and Cross-Kingdom Signalling in the Bacterial World*, Microbiology, 2007, 153, 3923-3938) and/or co-culture competitive species. As such, the methods and MCCs of the present invention are applicable to a wide variety of applications, e.g., including biomolecular catalysis, drug delivery, and tissue engineering.

Additional characteristics and features of the present invention will be further understood through reference to the following additional discussion and examples, which are provided by way of further illustration and are not intended to be limiting of the present invention.

Example 1

Figure 3:
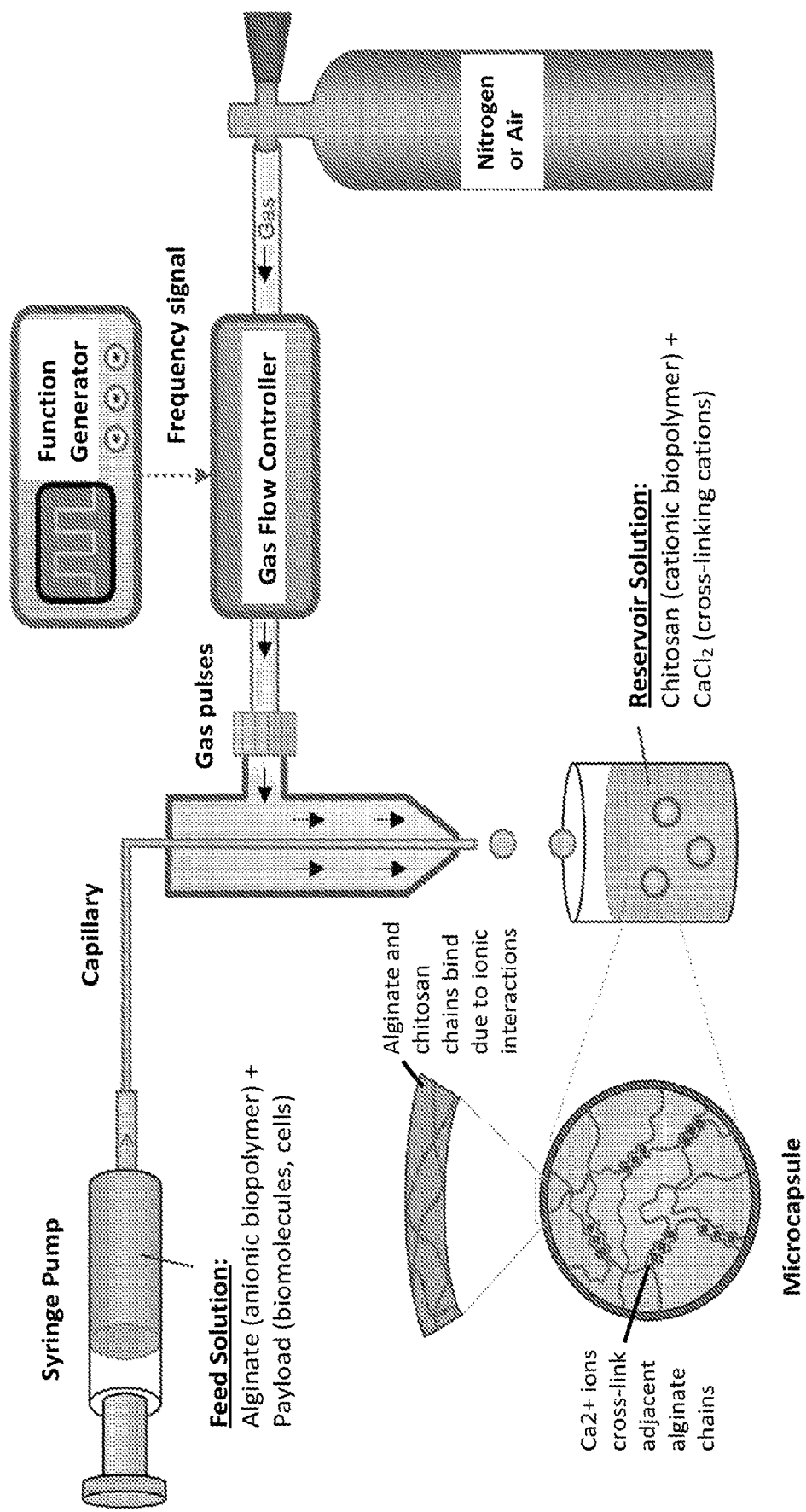
FIG. 3 illustrates schematically a system for synthesizing MCCs by a water-gas microfluidic technique in accordance with disclosed embodiments. Microdroplets bearing the anionic biopolymer (e.g., alginate) as well as payloads of interest are generated by flowing the aqueous solution through a capillary. Pulses of gas (nitrogen or air) are sent through the annular region around the capillary. The frequency of the pulses is controlled by the function generator. Uniform aqueous droplets emerge from the tip of the capillary, and these are introduced into an aqueous reservoir solution containing the cationic biopolymer (e.g., chitosan) as well as the salt of a divalent cation ($Ca^{2+}$). The droplets are thereby converted into microcapsules, with the shell being formed by electrostatic complexation between the anionic biopolymer and the cationic biopolymer while the core is further strengthened (e.g., by the $Ca^{2+}$-induced cross-linking of alginate chains).

Preparation of individual compartments. Individual microscale capsules were first prepared using a water-gas microfluidic setup as shown in FIG. 3. These capsules serve as the internal compartments in the MCC structure. Typical setups for droplet microfluidics use immiscible aqueous and oily phases, which are brought into contact at a T-junction or within a co-flow geometry (Shah, R. K. et al. *Designer Emulsions Using Microfluidics*, Mater. Today, 2008, 11, 18-27; Seemann, R. et al. *Droplet Based Microfluidics*, Rep. Prog. Phys., 2012, 75, 016601). In contrast, the setup utilized herein to form the polymer MCCs provides for oil-free droplet microfluidics, where instead of the oil (which is harmful to some biological systems), an inert gas (e.g., either air or nitrogen) was utilized (see, e.g., Ghaffarian, R. et al. *Chitosan-Alginate Microcapsules Provide Gastric Protection and Intestinal Release of ICAM-1-Targeting Nanocarriers, Enabling GI Targeting In Vivo*, Adv. Funct. Mater., 2016, 26, 3382-3393).

Figure 4:
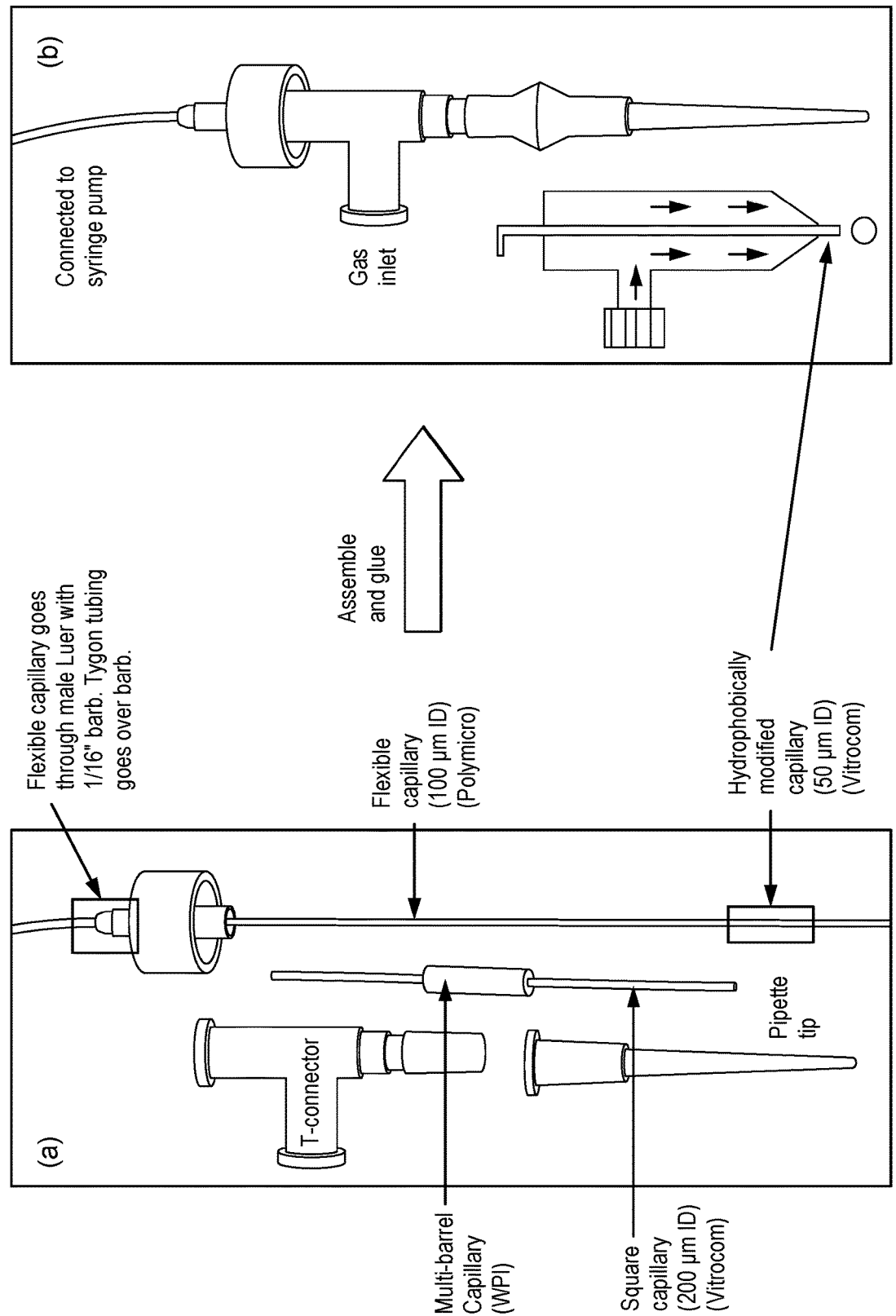
FIG. 4 are images of components of the microfluidic system shown in FIG. 3 and used to generate capsules and MCCs. Various components prior to assembly are shown in panel (a). The resulting device is shown in panel (b) after assembling and adhesively securing the components, with the corresponding portion of the setup shown in FIG. 3 reproduced in an inset in panel (b). The liquid emerges from the capillary with an inner diameter (ID), e.g., of about 50 µm.
Figure 5:
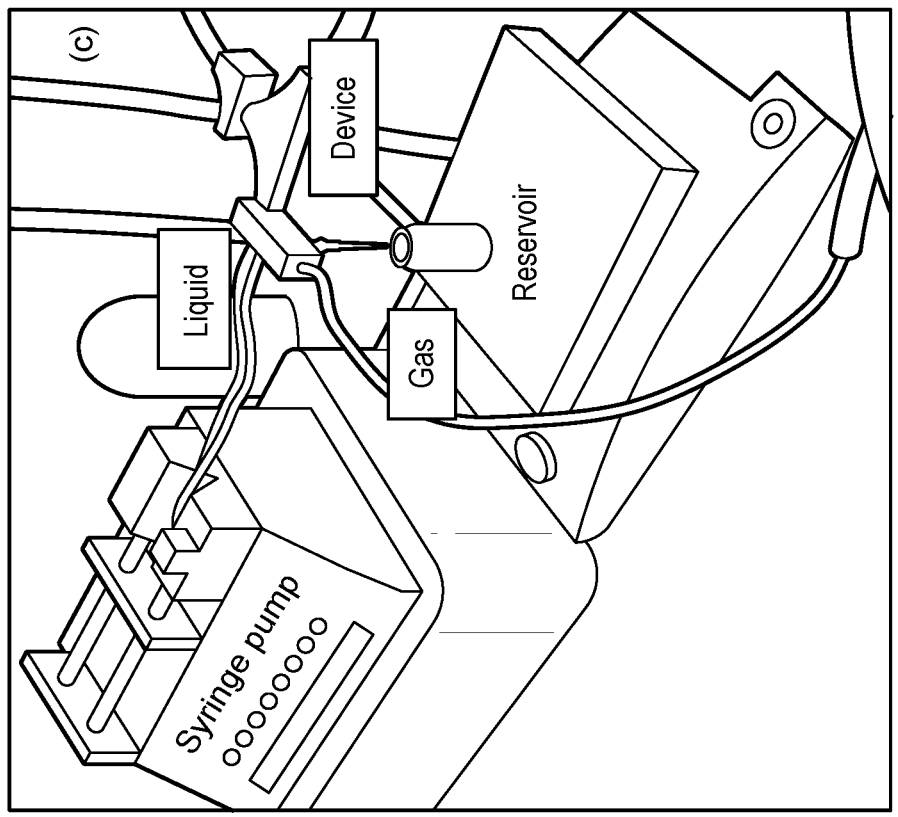
FIG. 5 illustrates a function generator and gas flow-regulator suitable for use with the disclosed invention, as shown in panel (a). The gas is sent as pulses at a pressure P, with each pulse over a duration of 0.1 s and with the spacing between pulses dictated by the frequency f, as shown in panel (b). An image of the system in operation is shown in panel (c), along with the syringe pump and collection reservoir or vial.
Figure 5:
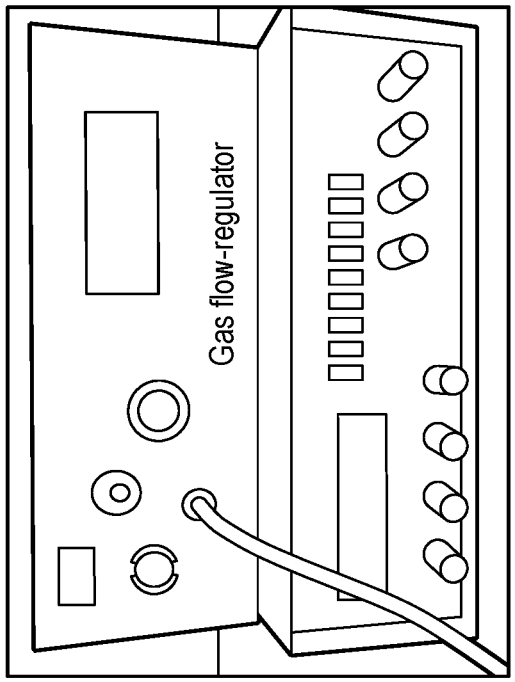
Figure 5:
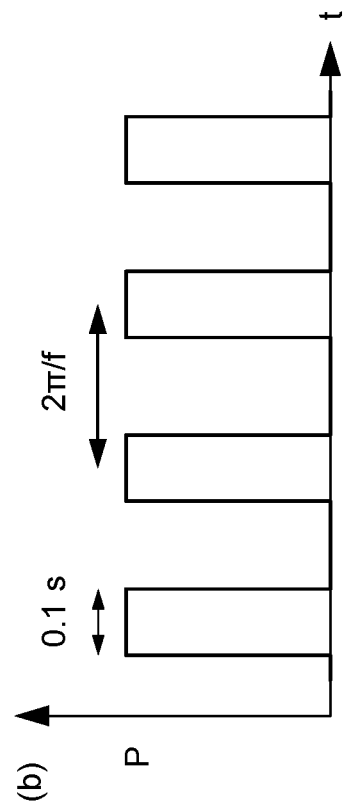

The droplet generator consists of an inner glass capillary having an inner diameter (ID) of about 50 µm, which was threaded through the end of a pipette tip (FIG. 4). The aqueous solution of interest was passed through this capillary, with the flow rate being controlled by a syringe pump. In the annular space surrounding the capillary, pulses of gas were dispatched by a function generator connected to a gas flow regulator (FIG. 3 and FIG. 5). The pulses were applied over a very short duration (0.1 s) while the duration between consecutive pulses was controlled by the pulsing frequency f (FIG. 5, panel (b)) (Lee, M. W. et al. *A Study of Ejection Modes for Pulsed—DC Electrohydrodynamic Inkjet Printing*, J. Aerosol Sci., 2012, 46, 1-6). The gas flows has a sheath around the tip of the inner capillary, and for every pulse of gas, an aqueous droplet was dislodged from the capillary tip. The use of a function generator enabled precise control over the size of droplets.

Aqueous droplets were converted into capsules by contact with the reservoir solution (FIG. 3). Several chemistries may be used in this context, e.g. with the biopolymer sodium alginate utilized. Alginate is an anionic polysaccharide that is compatible with biomolecules as well as biological cells (Lee, K. Y. and Mooney, D. J. *Alginate: Properties and Biomedical Applications*, Prog. Polym. Sci., 2012, 37, 106-126). As known in the art, alginate solutions can be converted to gels by addition of multivalent cations like $Ca^{2+}$ or $Sr^{2+}$; these cations form crosslinking zones called "egg-box" junctions between adjacent alginate chains. In the exemplary setup (FIG. 3), 2.25 wt % alginate was used in the droplet generator, while the reservoir contained 1 wt % of $CaCl_2$ and 1 wt % of chitosan. Chitosan is a cationic polysaccharide (Peniche, C. et al. *Chitosan: An Attractive Biocompatible Polymer for Microencapsulation*, Macromol. Biosci., 2003, 3, 511-520). The chitosan utilized had a low molecular weight of 5000 Da; it is an oligomer and is soluble at neutral pH (Bartkowiak, A. and Hunkeler, D. *Alginate-Oligochitosan Microcapsules: A Mechanistic Study Relating Membrane and Capsule Properties to Reaction Conditions*, Chem. Mater., 1999, 11, 2486-2492).

When the alginate-bearing droplets contact the reservoir solution, two processes occur. The anionic alginate and the cationic chitosan undergo electrostatic complexation (Bartkowiak, A. and Hunkeler, D. *Alginate-Oligochitosan Microcapsules: A Mechanistic Study Relating Membrane and Capsule Properties to Reaction Conditions*, Chem. Mater., 1999, 11, 2486-2492; Ghaffarian, R. et al. *Chitosan-Alginate Microcapsules Provide Gastric Protection and Intestinal Release of ICAM-1-Targeting Nanocarriers, Enabling GI Targeting In Vivo*, Adv. Funct. Mater., 2016, 26, 3382-3393), where the oppositely charged polymers bind together and form a gel. This process begins at the surface of the droplet, forming a shell around the droplet (FIG. 3), and proceeds inward. At the same time, the $Ca^{2+}$ ions in the solution also diffuse into the droplet and cross-link the alginate chains. The combination of the two processes results in the conversion of droplets into stable capsules.

The shell has distinct properties from the core (Ohkawa, K. et al. *Preparation and Characterization of Chitosan-Gellan Hybrid Capsules Formed by Self-Assembly at an Aqueous Solution Interface*, Macromol. Mater. Eng., 2004, 289, 33-40; Lee, H. Y. et al. *Biopolymer Capsules Bearing Polydiacetylenic Vesicles as Colorimetric Sensors of pH and Temperature*, Soft Matter, 2011, 7, 3273-3276; Dowling, M. B. et al. *Self-Destructing "Mothership" Capsules for Timed Release of Encapsulated Contents*, Langmuir, 2013, 29, 7993-7998; Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562; Ghaffarian, R. et al. *Chitosan-Alginate Microcapsules Provide Gastric Protection and Intestinal Release of ICAM-1-Targeting Nanocarriers, Enabling GI Targeting In Vivo*, Adv. Funct. Mater., 2016, 26, 3382-3393). The $Ca^{2+}$ ions tend to diffuse all the way through the droplet, resulting in the entire core becoming a gel. The chitosan, being a macromolecule, diffuses a shorter distance and is thus confined near the shell. After a certain incubation time in the reservoir (about 30 min), the capsules were washed with phosphate-buffered saline (PBS) and then resuspended in PBS.

Figure 6:
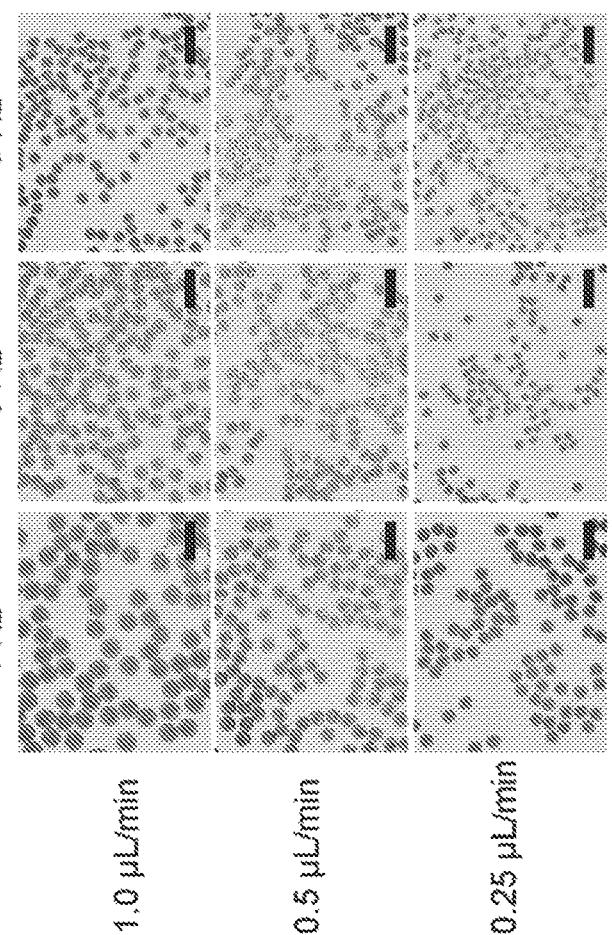
FIG. 6 illustrates the effect of liquid flow rate (Q) and gas pulse frequency (f) on the size of microcapsules. A plot of capsule diameter vs. frequency at three different flow rates is shown in panel (a). The values plotted are the means determined from image analysis and the error bars represent standard deviations about the mean. Up to frequency of ~6 Hz, the capsules are very uniform, with the standard deviations being <3%. The lines through the data are fit to Equation 1 (discussed below). Optical micrographs of typical capsules generated at different Q (0.25, 0.5, 1.0 µL $min^{-1}$) and f (1, 3, 5 Hz) are shown in panel (b), with all scale bars representing 500 µm.
Figure 6:
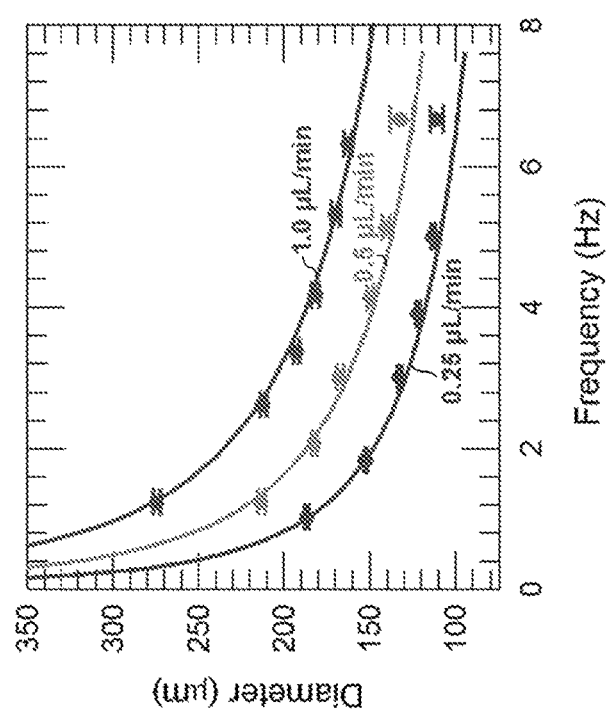

Since each droplet is converted into a capsule, the size of the droplets dictates the size of the capsules. Variables that affect droplet size include the feed (liquid) flow rate Q, which is controlled by the syringe pump, and the pulsing frequency f of the gas, which is controlled by the function generator and was varied between 1 to 7 Hz in the experiments. The effects of these two variables on capsule size are shown in FIG. 6. Capsule diameter was plotted against frequency for three different liquid flow rates, as shown in FIG. 6, panel (a). Optical micrographs of capsules obtained at specific conditions are shown in FIG. 6, panel (b). In all cases, the capsules were very uniform, with the polydispersities in their diameter being <3%. As shown in FIG. 6, panel (a), capsule size may be decreased by either lowering the liquid flow rate Q or by increasing the pulsing frequency f. These trends can be understood based on how Q and f affect the droplet volume. Assuming that every pulse of gas results in exactly one droplet (and hence one capsule), the droplet volume may be expressed as $V_{droplet}=Q/f$. The capsule is slightly smaller than the droplet due to shrinking, with $V_{capsule}=\alpha(V_{droplet})$ with $\alpha \leq 1$. In turn, the capsule diameter $d_{cap}$ can be calculated as:

$$d_{cap} = \left(\frac{6aV_{droplet}}{\pi}\right)^{1/3} = \left(\frac{6aQ}{\pi f}\right)^{1/3} \quad \text{(Equation 1)}$$

The lines in FIG. 6, panel (a), are fits of Equation 1 at each flow rate Q with a value of $\alpha=0.81$ for all three cases. An excellent match was seen between the predicted and measured capsule sizes for frequencies ranging from 1 to 6 Hz. Above 6 Hz, a slight discrepancy between the two sizes was seen, likely because droplets were no longer generated at the rate of one per pulse of gas. FIG. 6, panel (a), may be used to pre-determine the conditions (Q, f) needed to obtain capsules of any desired diameter, e.g. between about 100 µm to about 300 µm. This is an advantage provided by the function generator; without it, control over capsule size is decreased (see, e.g., Lee, M. W. et al. *A Study of Ejection Modes for Pulsed—Electrohydrodynamic Inkjet Printing*, J. Aerosol Sci., 2012, 46, 1-6). The data shown in FIG. 6, panel (a), were collected at a particular diameter of the capillary and at a specific gas pressure (14 psi). The pressure is set by the gas flow-regulator, and its value was chosen such that it was high enough to dislodge the liquid droplet, but not too high as to break the droplet into smaller units. Once this pressure is set, the capsule size may be readily controlled using Equation 1 regardless of the fluid properties.

Preparation of MCCs.

Figure 7:
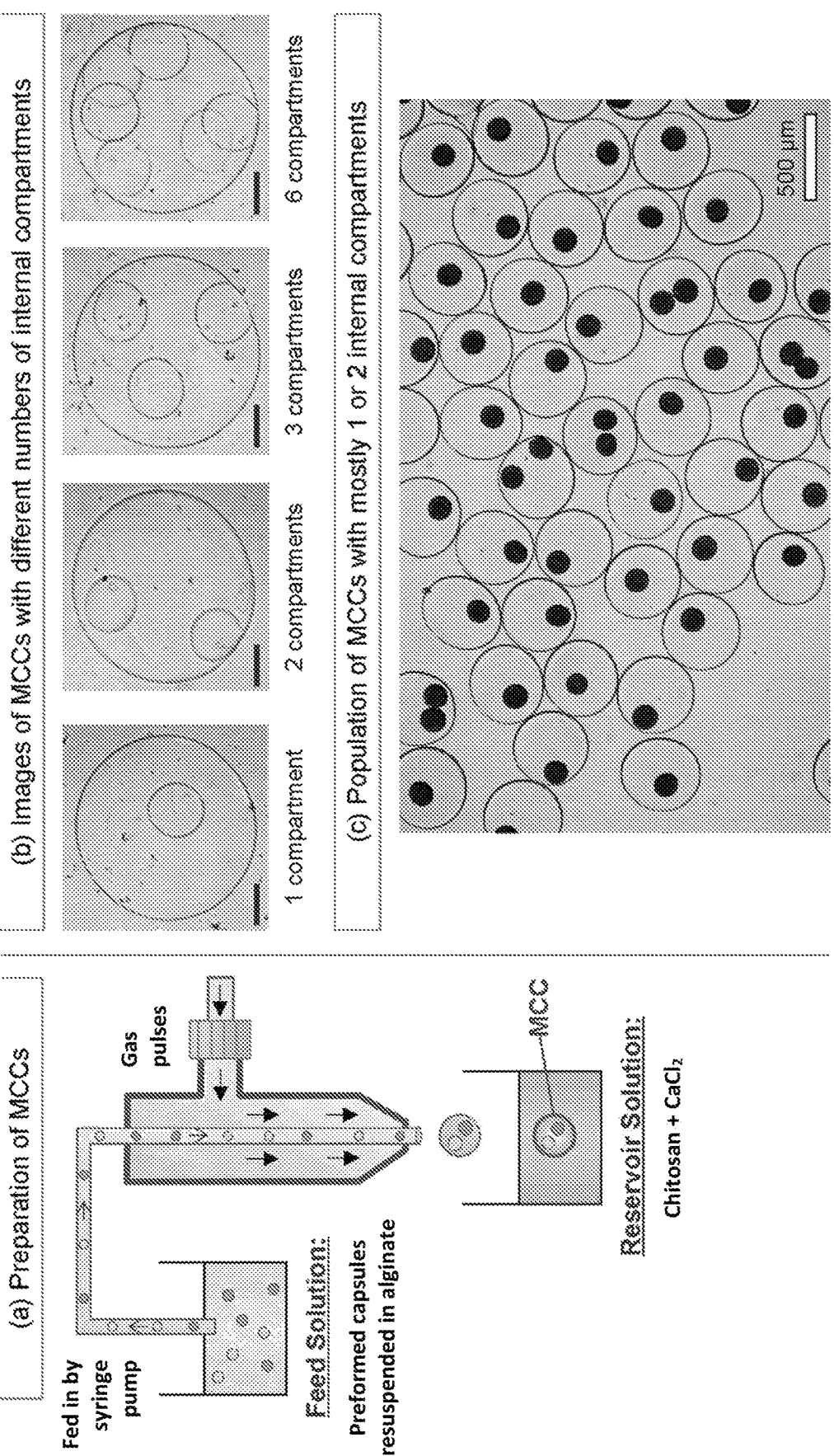
FIG. 7 illustrates the preparation and resulting images of exemplary MCCs. As shown in panel (a), preparation of MCCs via the water-gas microfluidic method is provided (as described in FIG. 3). A suspension of preformed capsules in an alginate solution was used as the liquid feed through the capillary. Gas pulses were used to dislodge uniform droplets from the tip of the capillary, and the droplets were then introduced into the reservoir solution containing chitosan and $Ca^{2+}$. The droplets were thereby converted into MCCs. Optical micrographs of individual MCCs with different numbers of substantially identical internal compartments are shown in panel (b), with scale bars in the images representing 100 µm. Optical micrographs of a population of MCCs having either one or two substantially identical internal compartments as shown in panel (c). The compartments all had a generally brown color because they contained magnetic $Fe_3O_4$ nanoparticles.

The formation of MCCs with inner compartments was demonstrated. The capsules formed as described above were utilized as the inner compartments (FIG. 7). Previously formed capsules from the prior step were suspended in PBS and 2 wt % alginate added. This capsule dispersion was utilized as the liquid feed into the gas-liquid droplet generator, as shown in FIG. 7, panel (a). The setup as described above was used (FIG. 3), with the same function generator, gas flow-regulator, and syringe pump. However, the diameter of the inner glass capillary was increased to 200 µm in order to accommodate the suspended capsules (forming the inner compartments). The reservoir composition was also identical to that described above (FIG. 3). Using this procedure, MCCs were formed, which were again washed and resuspended in PBS. MCCs with different numbers of inner compartments were achieved. FIG. 7, panel (b), shows optical micrographs of MCCs with one, two three, and six inner compartments. The diameter of the MCCs was about 400 µm, while the diameter of each inner compartment was about 100 µm. Thus, MCCs were readily formed with different internal architecture using the disclosed methods. The lumen of the MCCs surrounding the compartments was also an alginate gel, similar to the lumen of each compartment.

MCCs having a particular number of internal compartments may be readily sorted and isolated. In forming the MCCs, a dispersion of capsules in alginate solution was utilized as the feed to the droplet generator. The higher the concentration (number density) of capsules in solution, the greater the average number of compartments in a given droplet (and hence in the subsequent MCC). However, droplet generation is a stochastic process, and therefore there are many variants. For example, as shown in FIG. 7, panel (c), a population of MCCs that possess one or two internal compartments were constructed by using a moderate concentration of capsules in the feed. The compartments had a dark brown color due to the presence of magnetic $Fe_3O_4$ nanoparticles (MNPs, 10 nm diameter) in each of them. To separate or sort MCCs having a particular characteristic from a larger batch, the relatively large size of the MCCs was conveniently exploited, wherein they were large enough to be easily seen and manipulated individually using an optical microscope. Thus, for example, MCCs with exactly two internal capsules may be sorted manually from the above population (FIG. 7, panel (c)) using a pipette tip on a microscope slide. While this method is somewhat rudimentary, it was effective at the length scale studied in this experiment.

Figure 8:
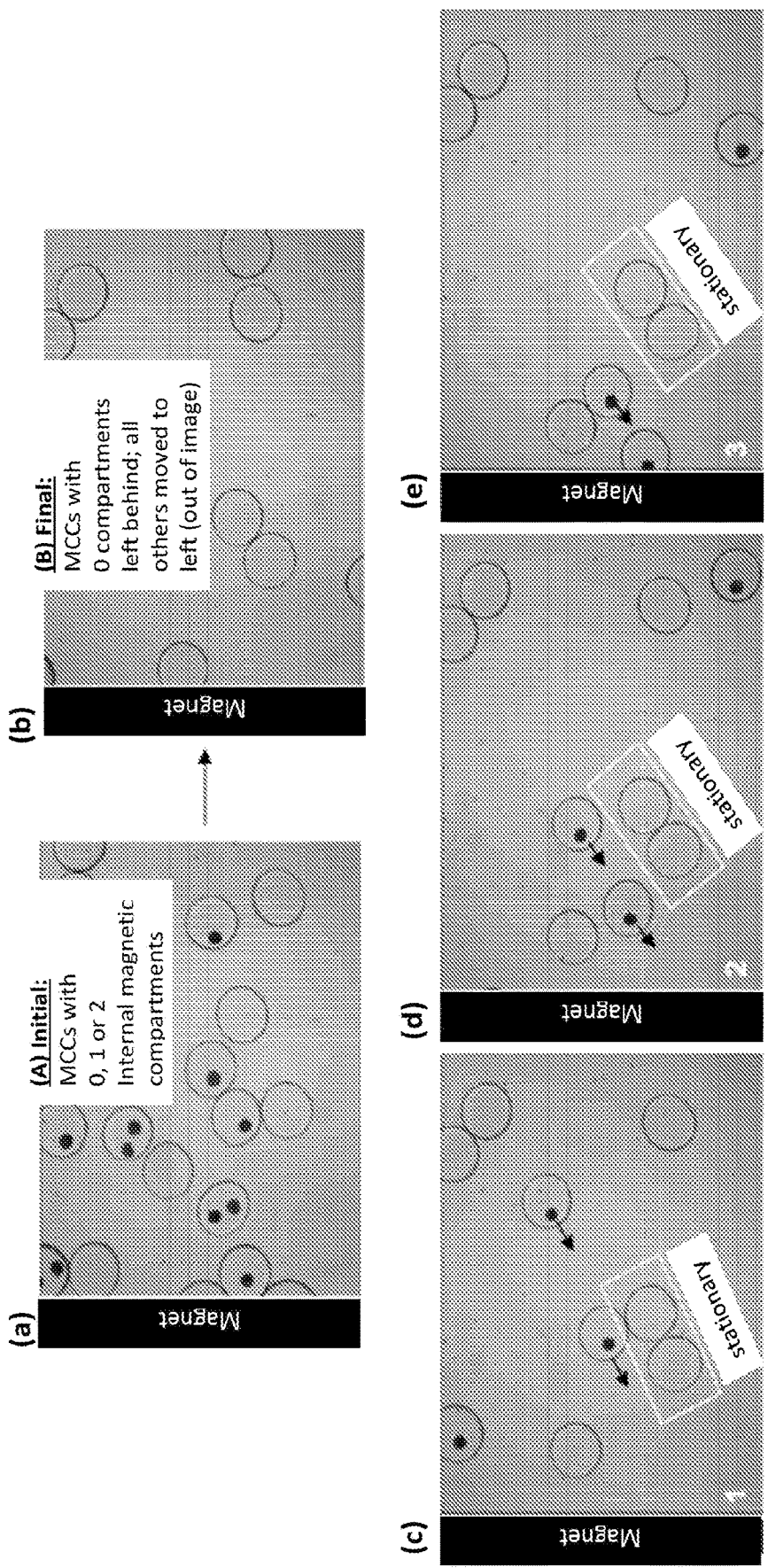
FIG. 8 illustrates a magnetic sorting of MCCs in accordance with disclosed embodiments. The images in panels (a-e) are still images from a video from the experiment. The initial and final images from the video are shown in panels (a) and (b). In the initial image shown in panel (a), a population of MCCs is provided in which some of the MCCs possessed internal compartments (smaller capsules) encapsulating magnetic nanoparticles. Some of the MCCs in the population did not have any internal compartment, while other MCCs had 1 or 2 such compartments. At t=0, a bar magnet was placed to the left of the volume containing the MCC population. This induced the MCCs with 1 or 2 internal compartments to move toward the magnet (and out of the field of view as shown in panel (b)) due to their magnetic properties. Thus, in the final image, only the MCCs lacking internal compartments were left behind (panel (b)). A succession of stills from the video are shown in panels (c), (d) and (e) and demonstrate the movement of the MCCs including internal compartments toward the magnet (shown by arrows in the images) relative to the stationary MCCs lacking any internal compartments (shown within boxes in the images).

When the population of MCCs is very large or if their sizes are much smaller, manual sorting may not be convenient or practical. In this case, two alternative approaches for sorting may be implemented. First, the MCCs may be sorted by density, given MCCs with different numbers of internal compartments have different densities. Sorting is then be done using a centrifuge. The density differences are accentuated by loading nanoparticles with a higher density, such as MNPs, in the core of each inner compartment. In that case, the number of compartments dictates the overall density of each MCC. A second related approach exploits the use of a magnetic field in the case of MNP bearing compartments. For example, an external bar magnet was utilized to isolate MCCs with one or two such compartments while leaving behind the capsules with no inner compartments (FIG. 8). Thereafter, a magnetic or density-based approach may be used to further separate the 2-compartment MCCs from the 1-compartment ones.

MCCs with distinct compartments. The utility of MCCs may be further exploited via the ability to load distinct contents in each compartment. In forming the original capsules, which serve as the inner compartments, any payload that is included along with the feed solution of alginate gets sequestered in the core of the capsules. The alginate solution is typically a thin, aqueous fluid at neutral pH, and its ionic strength may also be adjusted to physiological levels (150 mM). Thus, this solution is compatible with a wide variety of biological payloads, including proteins, nucleic acids, microorganisms, and mammalian cells. Based on studies with biopolymer capsules (see, e.g., Lee, H. Y. et al. *Biopolymer Capsules Bearing Polydiacetylenic Vesicles as Colorimetric Sensors of pH and Temperature*, Soft Matter, 2011, 7, 3273-3276; Dowling, M. B. et al. *Self-Destructing "Mothership" Capsules for Timed Release of Encapsulated Contents*, Langmuir, 2013, 29, 7993-7998; Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562; Ghaffarian, R. et al. *Chitosan-Alginate Microcapsules Provide Gastric Protection and Intestinal Release of ICAM-1-Targeting Nanocarriers, Enabling GI Targeting In Vivo*, Adv. Funct. Mater., 2016, 26, 3382-3393; Zargar, A. et al. *Constructing 'Quantized Quorums' to Guide Emergent Phenotypes Through Quorum Quenching Capsules*, Biotechnol. Bioeng., 2017, 114, 407-415; Ohkawa, K. et al. *Preparation and Characterization of Chitosan-Gellan Hybrid Capsules Formed by Self-Assembly at an Aqueous Solution Interface*, Macromol. Mater. Eng., 2004, 289, 33-40; Peniche, C. et al. *Chitosan: An Attractive Biocompatible Polymer for Microencapsulation*, Macromol. Biosci., 2003, 3, 511-520), it has been determined that the outer shell of these capsules allows small molecules and ions to pass through, but acts as a barrier to any species that are at the nanoscale or larger. For example, various nanoscale entities have been encapsulated including: enzymes or fusion proteins with molecular weights of 80 kDa and higher, i.e., a radius of gyration $R_g$ of about 10-30 nm) (Dowling, M. B. et al. *Self-Destructing "Mothership" Capsules for Timed Release of Encapsulated Contents*, Langmuir, 2013, 29, 7993-7998; Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562; Ghaffarian, R. et al. *Chitosan-Alginate Microcapsules Provide Gastric Protection and Intestinal Release of ICAM-1-Targeting Nanocarriers, Enabling GI Targeting In Vivo*, Adv. Funct. Mater., 2016, 26, 3382-3393), inorganic nanoparticles with sizes of a few nm, and liposomes or vesicles with sizes of about 100 nm (Lee, H. Y. et al. *Biopolymer Capsules Bearing Polydiacetylenic Vesicles as Colorimetric Sensors of pH and Temperature*, Soft Matter, 2011, 7, 3273-3276; Dowling, M. B. et al. *Self-Destructing "Mothership" Capsules for Timed Release of Encapsulated Contents*, Langmuir, 2013, 29, 7993-7998). Such nanoscale entities remain entrapped in the capsule lumen and do not escape through the shell into the external medium. In addition, any or all of these payloads (and/or other payloads) may be readily mixed or substituted in the MCCs.

To demonstrate multiple compartments with distinct payloads in an MCC, two kinds of fluorescent colloids were employed, which exhibit green and red fluorescence, respectively. Both particles had diameters of about 800 nm. The microfluidic setup described above (FIG. 3) was utilized to produce one set of capsules with green fluorescent particles encapsulated therein. Then, another batch of capsules was produced with red fluorescent particles encapsulated therein. The two batches of capsules were then combined in an alginate solution, which was used as the feed to produce MCCs (FIG. 7). The resulting MCCs are shown unsorted in FIG. 9, panel (a). Optical micrographs are shown in brightfield, fluorescence, and combined mode. The observed MCCs have one or two inner compartments, which was the result of using a moderate concentration of red and green capsules in the feed solution. All combinations are seen in the image, including MCCs with two red, two green, one red and one green, only one red, and only one green compartment. A few MCCs with more than two compartments were also observed. In all cases, there was no leakage of fluorescence from the distinct compartments to the lumen of the MCC or to an adjacent compartment, indicating that the particles remained localized within their respective compartments.

Figure 9:
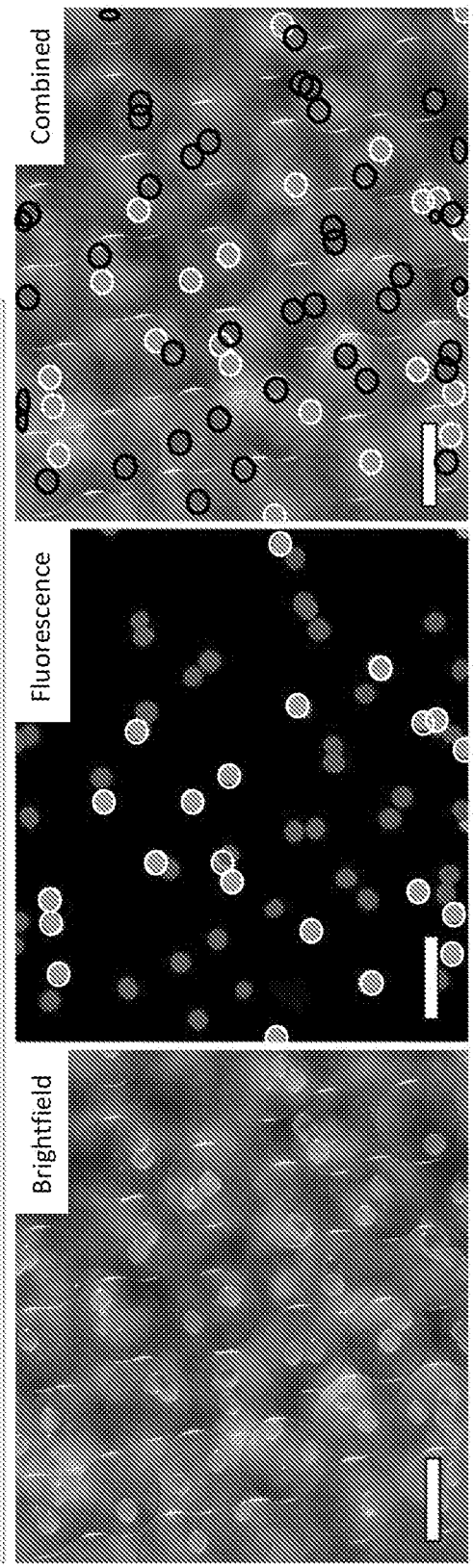
FIG. 9 are images of MCCs with internal compartments bearing distinct payloads. Images in panel (a) illustrate compartments having either green fluorescent (identified with white circles in the fluorescence and combined images) or red fluorescent colloidal particles (800 nm diameter) (identified with black circles in the combined image), with scale bars representing 500 µm. Images in panel (b) illustrate compartments have two strains of E. coli that express either green fluorescent protein (GFP) (identified with white circles in the fluorescence and combined images) or red fluorescent protein (RFP) (identified with black circles in the fluorescence and combined images), with scale bars representing 1000 µm. In each of panels (a) and (b), the left and middle images are shown in brightfield and fluorescence mode, respectively, and the two are combined in the right image.
Figure 9:
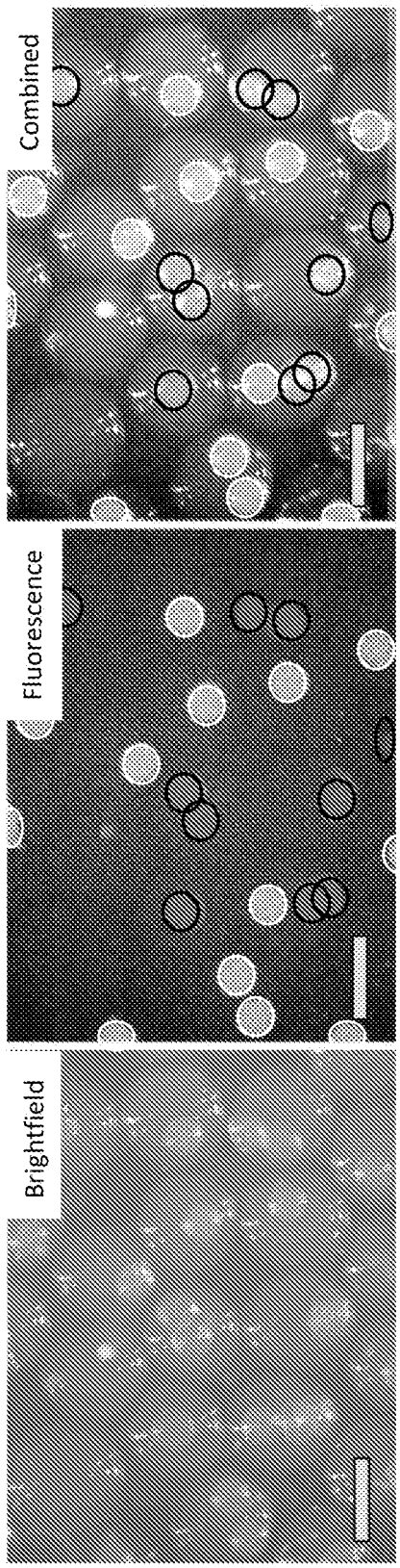

Next, MCC synthesis was performed with two distinct strains of bacteria (*E. coli*). Both strains were genetically engineered to detect a signaling molecule called autoinducer 2 (AI-2) and to respond by activating the genes for specific fluorescent proteins (Wang, L. et al. *luxSDependent Gene Regulation in Escherichia coli K-12 Revealed by Genomic Expression Profiling*, J. Bacteriol., 2005, 187, 8350-8360; Wu, H. C. et al. *Autonomous Bacterial Localization and Gene Expression Based on Nearby Cell Receptor Density*, Mol. Syst. Biol., 2013, 9, 636; Tsao, C. Y. et al. *Autonomous Induction of Recombinant Proteins by Minimally Rewiring Native Quorum Sensing Regulon of E. coli*, Metab. Eng., 2010, 12, 291-297). One bacteria strain was engineered to produce green fluorescent protein (GFP) while the other strain was engineered to produce red fluorescent protein (RFP). AI-2 is a molecule that is synthesized by bacteria and involved in bacterial quorum sensing. However, in this experiment, synthetic AI-2 was added to the solution and used as a trigger to turn on bacterial responses, wherein the bacteria utilized mutants that could not synthesize their own AI-2(id.). Capsules were again first made containing each strain of *E. coli*., The two sets of capsules were then combined to produce MCCs. These MCCs are shown in FIG. 9, panel (b), with the bacteria localized in distinct internal compartments. In the presence of growth (LB) medium, when placed on a shaker at 37° C. the bacteria grew and formed colonies inside their compartments. Moreover, when AI-2 was added to the medium, the bacteria were induced to fluoresce. FIG. 9, panel (b), shows MCCs with combinations of red and green fluorescent compartments, much like the MCCs with particles (FIG. 9, panel (a)). The bacteria were confined to their specific compartments and did not come into contact with each other. Images were taken 1-2 h after the AI-2 was added. Thus, the MCCs permitted simultaneous co-culture of two bacterial strains in their specific microenvironments.

MCCs used to conduct a bacterial cascade process. FIG. 9, panel (b) shows the successful encapsulation and cultivation of biological cells in their own compartments within MCCs. Next, a cascade process involving such cells was evaluated, wherein a change occurring in one compartment of the MCC was transduced into a response in an adjacent compartment. For this, two genetically engineered *E. coli* strains were used that can participate in quorum sensing (QS). QS is an important process in bacterial communication wherein the behavior (phenotype) of a bacterial population changes when a minimum cell density (quorum) is reached (Williams, P. *Quorum Sensing, Communication and Cross-Kingdom Signalling in the Bacterial World*, Microbiology, 2007, 153, 3923-3938; Pereira, C. S. et al. *AI-2-Mediated Signalling in Bacteria*, FEMS Microbiol. Rev., 2013, 37, 156-181). Changes in phenotype caused by QS include the expression of virulence factors or the formation of bacterial biofilms. Bacteria produce and release signaling molecules such as AI-2 that regulate QS. The ability of capsules and liposomes to interfere with bacterial QS pathways has been a topic of continued interest (see, e.g., Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562; Lentini, R. et al. *Integrating Artificial with Natural Cells to Translate Chemical Messages that Direct E. coli Behaviour*, Nat. Commun., 2014, 5, 4012).

Figure 10:
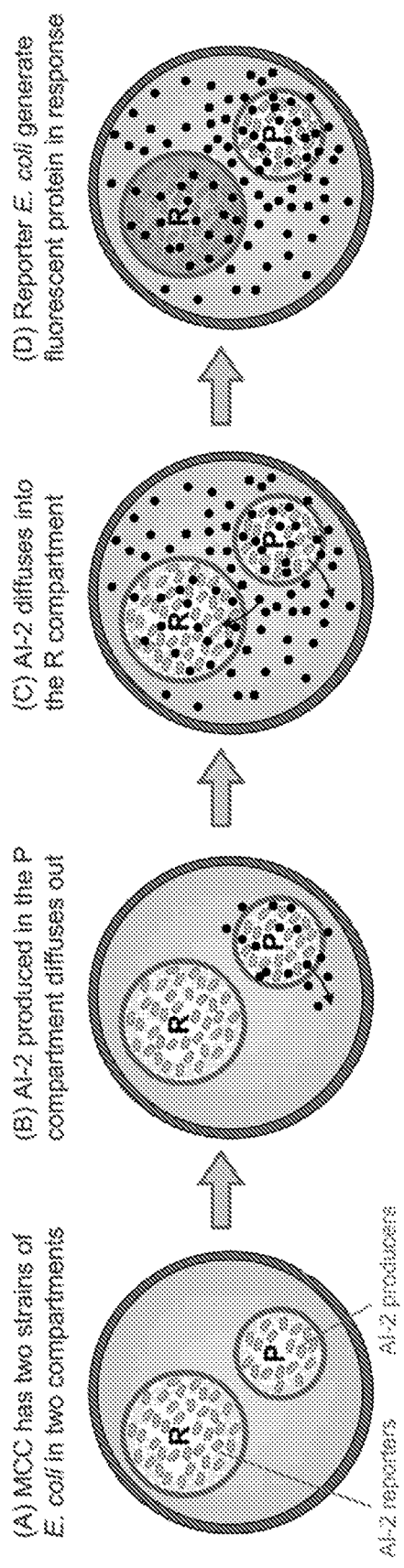
FIG. 10 illustrates schematically a bacterial cascade process using MCCs in accordance with the present invention. As shown schematically in panel (a), an MCC is initially provided in which two strains of *E. coli* are encapsulated in two distinct compartments. The strain in the P compartment is an AI-2 producer while the strain in the R compartment is an AI-2 reporter. Neither compartment is fluorescent at this stage. As shown in panel (b), as the bacteria grow, AI-2 (identified by black dots) is synthesized in the P compartment. The AI-2 diffuses out into the capsule lumen. As shown in panel (c), the AI-2 then diffuses into the R compartment, where it turns on the reporter bacteria. As shown in panel (d), in turn, the reporter *E. coli* synthesize the fluorescent protein VENUS, and thus the entire compartment appeared green under a fluorescence microscope.
Figure 11:
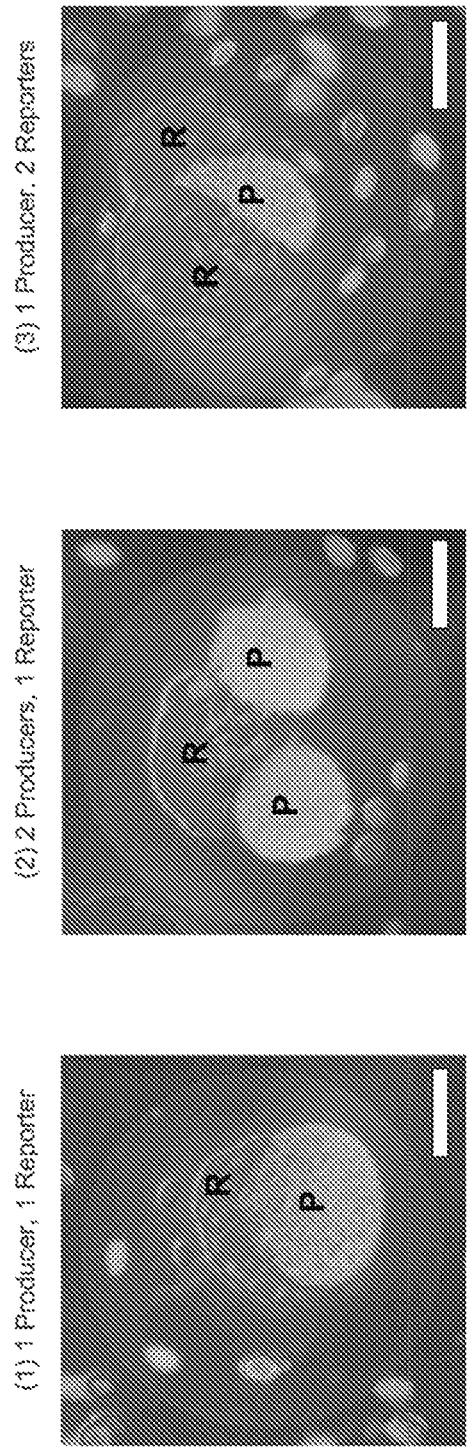
FIG. 11 are combined brightfield and fluorescence microscopy images for individual MCCs with different arrangements of P and R compartments (as described in FIG. 10). In panels (a), (b) and (c), there are at least one P and one R compartments in the MCC, wherein the P compartments were deliberately constructed to be slightly smaller than the R compartments. As expected, the images showed fluorescence in the R compartment but not the P compartments. Scale bars in panels (a), (b) and (c) represent 250 µm.

Two bacterial strains were chosen for experimentation. One strain, *E. coli* BL21, is an AI-2 producer; compartments in the MCC with this strain are labeled P (FIG. 10 and FIG. 11). The other strain, *E. coli* W3110, is an AI-2 reporter with compartments with this strain labeled R. The reporter *E. coli* are mutants that cannot synthesize their own AI-2, but create a green-yellow fluorescent protein called VENUS in response to AI-2 (Dowling, M. B. et al. *Self-Destructing "Mothership" Capsules for Timed Release of Encapsulated Contents*, Langmuir, 2013, 29, 7993-7998; Gupta, A. et al. *Encapsulated Fusion Protein Confers "Sense And Respond" Activity to Chitosan-Alginate Capsules to Manipulate Bacterial Quorum Sensing*, Biotechnol. Bioeng., 2013, 110, 552-562). MCCs with combinations of R and P compartments were constructed. For ease of identification, the R compartments were deliberately synthesized at a slightly larger size than the P compartments.

The experiment over the course of time is schematically depicted in FIG. 10. At time t=0, the MCCs are placed in growth media at 37° C. (FIG. 10, panel (a)), at which stage neither compartment of the MCC showed fluorescence. As time progresses (t=4 to 6 h), the cells grew and formed small microcolonies in the compartments. AI-2 was produced in the P compartments and diffused out and into the MCC lumen (or corresponding "cytoplasm") and from there into the R compartments (FIG. 10, panels (b) and (c)). Note that AI-2 is a small molecule with a molecular weight of 193 Da and thus can readily pass through capsule shells. When a sufficient concentration of AI-2 was reached in the R compartments (t>12 h), the reporter *E. coli* responded by creating the fluorescent VENUS protein (FIG. 10, panel (d)). Thus, a fluorescence signal was expected in the R compartments (but not the P ones) after an induction time. This was exactly what was observed by fluorescence microscopy. FIG. 11 show superpositions of fluorescence and brightfield images taken after 24 h of culture. The fluorescence signal from VENUS showed as a green color due to the filter settings on the microscope. The images are of single capsules with different combinations of P and R compartments. FIG. 11, panel (a), shows an MCC having one P compartment and one R compartment. (Note that the R compartment is behind the P compartment and hence mostly obscured from view). FIG. 11, panel (b), shows an MCC having two P compartments and one R compartment. FIG. 11, panel (c), shows an MCC having two R compartments and one P compartment. In all cases, bright fluorescence in the R compartment(s) but not in the P compartment was observed.

Interestingly, in 24 h, the bacteria rapidly proliferated such that some of their microcolonies could no longer be contained within their home compartment. As a result, some colonies were seen in the lumen of the MCC. Similar findings of microbes outgrowing their initial confines and leaking out into the external medium have been reported for alginate capsules encapsulating yeast (Kim, B. J. et al. *Cytoprotective Alginate/Polydopamine Core/Shell Microcapsules in Microbial Encapsulation*, Angew. Chem., Int. Ed., 2014, 53, 14443-14446). In the present case, the presence of the distally spaced microcolonies in the lumen demonstrated the distances by which AI-2 travels by diffusion over the period of observation. Overall, it was demonstrated that bacteria remain viable owing to their ability to abstract energy and nutrients from the surrounding medium (FIG. 11). Furthermore, they continue to be capable of making and transducing signaling molecules. This demonstration thus illustrated that small molecules may be transmitted and received by viable cells contained in each compartment, revealing molecular "crosstalk" between the adjacent compartments.

Discussion.

A simple, scalable technique for synthesizing MCCs is demonstrated herein. The disclosed methods address many of the problems associated with prior approaches. Moreover, common and inexpensive biopolymers (e.g., alginate, chitosan) may be utilized as precursors in the disclosed methods, which are biocompatible and widely used in biochemical and cellular applications. A water-gas microfluidic technique is provided for generating biopolymer-containing aqueous droplets, which are then converted to capsules upon contact with a reservoir solution. No immiscible phase (oil) is required in the entire process, which greatly simplifies isolation, cleanup and purification of the capsules. To form the capsules, the electrostatic complexation of oppositely charged biopolymers is exploited, along with ionic cross-linking. These processes are mild and do not involve any covalent bond formation. Thus, they are biologically benign and compatible with labile payloads such as enzymes and microbial or eukaryotic cells. The above capsules may then be combined in a second step using the same microfluidic setup to produce MCCs. The disclosed approach provides precise control over the number and size of the inner compartments in the MCCs and most importantly for some applications over the contents of each compartment. Compartments with enzymes, colloidal particles, and biological cells, may be readily juxtaposed within a given MCC.

A cascade process between strains of E. coli in separate compartments of the MCCs was demonstrated. AI-2 generated by a producer strain of *E. coli* in one compartment diffused over to the neighboring compartment(s), where a reporter strain of E. coli generated a fluorescent response.

The exemplary experiment demonstrates that bacteria (or other cells) can be cultured in individual compartments of an MCC, just like in a Petri dish. For bacteria to thrive and grow, it is important that each compartment remains permeable to small molecules such as nutrients from growth media but remains impermeable to nanoscale entities such as enzymes or nanoparticles. The MCCs of the present invention exhibit such features. Further, the experiments herein demonstrate that cross-talk between different microbial species may be studied using the disclosed MCCs. To the inventors' knowledge, this is the first example of a cellular cascade process within an artificial-cell construct. Thus, the disclosed methods and MCCs are applicable in a wide variety of contexts. For example, in terms of physical and chemical studies, aqueous catalytic processes involving distinct catalysts (e.g., nanoparticles) may be sequestered in different compartments. In terms of biological studies, MCCs may be utilized to evaluate the co-culture of competitive species and/or cross-talk between one kingdom of microorganisms to another.

Materials and Methods

Materials and Chemicals.

The following chemicals were obtained from Sigma-Aldrich (St. Louis, Mo.): the biopolymers, sodium alginate (from brown algae, medium viscosity) and chitosan oligosaccharide lactate (5000 Da, degree of deacetylation >90%); the nonionic surfactant, Pluronic F127; and the inorganic salt, calcium chloride dihydrate. PBS and LB broth were obtained from Life Technologies (Waltham, Mass.). Magnetic nanoparticles (EMG 304) with a nominal diameter of 10 nm were obtained as an aqueous dispersion (4.5 vol % particles) from Ferrotec (Santa Clara, CA). Fluorescently-labeled green and red microparticles (0.7-0.9 μm diameter) were purchased from Spherotech (Lake Forest, IL) as an aqueous dispersion (1% w/v of particles).

Device fabrication. The microfluidic device was fabricated as shown schematically in FIG. 3 and with images of components shown in FIG. 4. A seven-barrel glass capillary (1.5 cm long) from World Precision Instruments (Sarasota, FL) was inserted into the male of a Luer adapter tee (Cole-Parmer, EW-45508-85). A 5 cm-long square capillary from Vitrocom (8320, with a 200 mm ID) was then inserted into the center of the seven-barrel capillary, and the whole setup was sealed by an epoxy adhesive (Devcon 5-min epoxy). Another glass capillary from Vitrocom (CV0508, with a 50 mm ID) was hydrophobically modified according to prior methods (Jiang, K. Q. et al. *Microfluidic Generation of Uniform Water Droplets Using Gas as the Continuous Phase*, J. Colloid Interface Sci., 2015, 448, 275-279). This capillary was inserted into a flexible capillary (Polymicro, TSP100200, polyimide-coated, and with a 100 mm ID) and sealed by epoxy. This flexible capillary was then threaded through the square capillary on one end and on the other end through a male Luer syringe connector with 1/16 in. hose barb (Cole Parmer, EW-45505-00). The extruded piece of the flexible capillary on the side of the barb was then inserted and epoxied into a piece of TYGON® tubing (Cole Parmer, EW-06509-13). A P1000 plastic pipette was cut to encase around the capillary apparatus to focus the gas stream, then sealed with epoxy. The nesting of multiple capillaries over a range of sizes was done to ensure that the smallest capillary (50 mm) was centered within the device, so that the gas flowed uniformly around its tip. It is through the tip of this smallest capillary that the liquid droplets emerged. Also, the nesting eliminated any vibration of this capillary due to the gas flow.

The device to fabricate the MCCs was relatively simple. Instead of the four capillaries as described above, only two were provided for this case. The seven-barrel glass capillary was used again. A circular capillary from Vitrocom (CV2033 with a 200 mm ID) was hydrophobically modified as per previous methods (Jiang, K. Q. et al. *Microfluidic Generation of Uniform Water Droplets Using Gas as the Continuous Phase*, J. Colloid Interface Sci., 2015, 448, 275-279). This was inserted into the center of the seven-barrel capillary. One end of the above circular capillary was then directly threaded into the male Luer syringe connector with 1/16 in. hose barb. TYGON® tubing was then capped over the barb, and the entire setup was sealed by epoxy.

In addition to the above capillary device, the setup (FIG. 3 and FIG. 4) included an adjustable syringe pump for the liquid feed (NE-1002X; Pump Systems Inc., Farmington, N.Y.), a gas flow-regulator (FIG. 5) (Techon Systems, Germantown, WI), a function generator (BK Precision, Yorba Linda, CA), and a cylinder of compressed air or nitrogen (AirGas, Radnor, Pa.). The settings for gas flow were set at timed pulses (P4) over 0.1 s, with consecutive pulses separated by the pulsing frequency f (FIG. 5, panel (b)). The pressure of the gas was set at a constant value of 14 psi. The gas output was connected to the other end of the TYGON® tubing from the capillary device. A disposable syringe was connected to the TYGON® tubing through a Luer lock. A piece of paper towel wetted with water was folded into the syringe to humidify the gas stream entering the device.

Synthesis of inner capsules and MCCs. For bare capsules, the feed solution consisted of 2.25 wt % alginate dissolved in PBS and it was filtered through 0.45 μm cellulose syringe filters (Millipore, Burlington, MA.) prior to use. The feed flow rate was varied between 0.25 to 1 μL min$^-$ (FIG. 3) while the pulsing frequency of the gas was varied between 1 to 7 Hz. Droplets were introduced into a reservoir solution consisting of 1 wt % chitosan, 1 wt % $CaCl_2$ and 0.3 wt % Pluronic F127. The reservoir was held on an adjustable stage (FIG. 5, panel (c)) so that the vertical distance between the capillary tip and the reservoir could be varied (with the distance maintained at about 2 in.). Once the droplets entered the reservoir, they were incubated for a period of about 30 min, whereupon they were converted to capsules. The presence of the Pluronic surfactant in the reservoir solution ensured that the droplets became immersed in the solution rather than collecting on the liquid surface. After formation, the capsules were washed three times with PBS and then resuspended in PBS.

For preparing the magnetic capsules, the feed consisted of alginate with the EMG 304 nanoparticles. To prepare this feed, 1.5 g of 3 wt % alginate solution was combined with 0.5 g of the EMG 304 dispersion diluted 10× with PBS (final alginate concentration was 2.25 wt % as before; final concentration of the magnetic particles was 0.05 wt %). Similarly, for preparing fluorescent capsules, 1.8 g of 2.5 wt % alginate was combined with 0.2 g of the dispersion of fluorescent microparticles (red or green). For preparing capsules containing bacterial cells, 1.5 g of 3 wt % alginate solution was combined with 0.5 g of the cell pellet.

For preparing MCCs, the capsules were resuspended in a 2 wt % alginate solution, and this suspension was used as the feed. The number density of capsules in this suspension was varied from 1000 to 10000 capsules per mL. The feed flow rate in this case was between 10 to 60 μL min$^{-1}$ while the pulsing frequency of the gas was again between 1 to 7 Hz. Droplets bearing capsules were introduced into a reservoir with identical composition as described above. Following an incubation time of 30 min, the resulting MCCs were washed three times with PBS and then resuspended in PBS.

Image Analysis.

Bright-field and fluorescence microscopy on the capsules and MCCs was performed using an Olympus MVX10® MACROVIEW™ fluorescence stereomicroscope equipped with a DP72 camera. Images were taken with red and green filter sets as well as in brightfield mode, and these were overlaid using ADOBE PHOTOSHOP® to visualize both colors simultaneously.

Cell Culture.

Two types of *E. coli* reporter strains were used: W3110 (DluxS)+pCT6+pET-dsRed for red fluorescent expression and W3110 (DluxS, DlsrFG) +pCT6 +pET-GFPuv for green fluorescent expression. BL21 (LuxS+) was used as AI-2 producers, and W3110 (DluxS, DlsrFG)+pCT6+pET-Venus was used as reporters of AI-2. Plasmid constructs are described by Tsao et al. (Tsao, C. Y. et al. *Autonomous Induction of Recombinant Proteins by Minimally Rewiring Native Quorum Sensing Regulon of E. coli*, Metab. Eng., 2010, 12, 291-297). All *E. coli* strains were grown in LB medium at 37° C. and 250 rpm until an optical density (at 600 nm) of 0.4 was reached. For the Venus-producing strain alone, the medium was supplemented with kanamycin and ampicillin at 50 μg mL$^{-1}$ per antibiotic). Subsequently, cultures were centrifuged at 3900 rpm for 7 min and resuspended in 0.5 g of PBS. Once encapsulated, the capsules were shaken at 37° C. to observe the bacterial responses.

Example 2

The construction of MCCs encapsulating *E. coli* and Caco-2 cells in their own compartments was demonstrated. Individual capsules were prepared using a water-gas microfluidic setup as described above (FIG. 3).

Cell Culture.

Caco-2 human colon carcinoma cell line was purchased from the American Type Culture Collection (Rockville, Md.) and grown in 75 cm$^2$ flasks in an incubator at 37° C. with 5% $CO_2$ and 95% relative humidity. Cells were cultured and maintained in Dulbecco's modified Eagle's medium (DMEM, GIBCO®) supplemented with 10% heat-inactivated fetal bovine serum (FBS, GIBCO®) and 10 μg ml$^{-1}$ PenStrep (GIBCO®). The cells were passaged when reached 80% confluence. *E.coli* strain W3110 with dsRed-Express gene region which expresses red fluorescence as the bacteria metabolizes was used and grown in LB medium at 37° C. and 250 rpm in an incubator shaker. Cells were re-inoculated in 1:100 dilution from overnight cultures and induced after 2 hours.

Encapsulation of Cells and Construction of MCCs.

The encapsulation methodology was adapted from the protocol as described above. Sodium alginate was dissolved to a final concentration of 2.0 wt % in 1× phosphate buffered saline (PBS, pH 7.4). The alginate solution was sterilized using UV light for 12 hours prior to use. For encapsulation, cells were collected by centrifugation after reaching mid-logarithmic growth ($OD_{600}$ 0.6 for *E. coli*, 2×10$^6$ cells/mL for Caco-2) and suspended in alginate solution to final concentration of 1.5 wt %. The cell-alginate mixture was extruded through a glass capillary (50 μm diameter for *E. coli*, 200 μm diameter for Caco-2) and sheared from the tip by a downward air pulse of 6 psi at a frequency of 4 Hz. Droplets were collected in a reservoir solution consisting of 1.0 wt % oligochitosan (<3000 Da), 100 mM $CaCl_2$ and incubated for 30 minutes. The capsules were washed three times with 1× PBS. After the wash, MCCs were constructed by resuspending the capsules containing *E. coli* and Caco-2 in 2.0 wt % alginate solution which was used as the feed solution. The suspension was added drop-wide to 100 mM $CaCl_2$ solution using a syringe needle (16G). After 30 minutes of incubation, MCCs were washed three times with 1x PBS and incubated in DMEM at 37° C. with 5% $CO_2$ and 95% relative humidity.

Image Analysis.

LIVE/DEAD® Viability/Cytotoxicity Kit (ThermoFisher Scientific, Waltham, Mass.) which gives green fluoresce to live mammalian cells was used to dye Caco-2 cells in MCCs for image analysis. Bright field and fluorescence images were taken using Zeiss Axiovert 135TV with red and green filters. The Zeiss LSM-310 laser-scanning microscope with FRP filters was used for confocal images.

Figure 12:
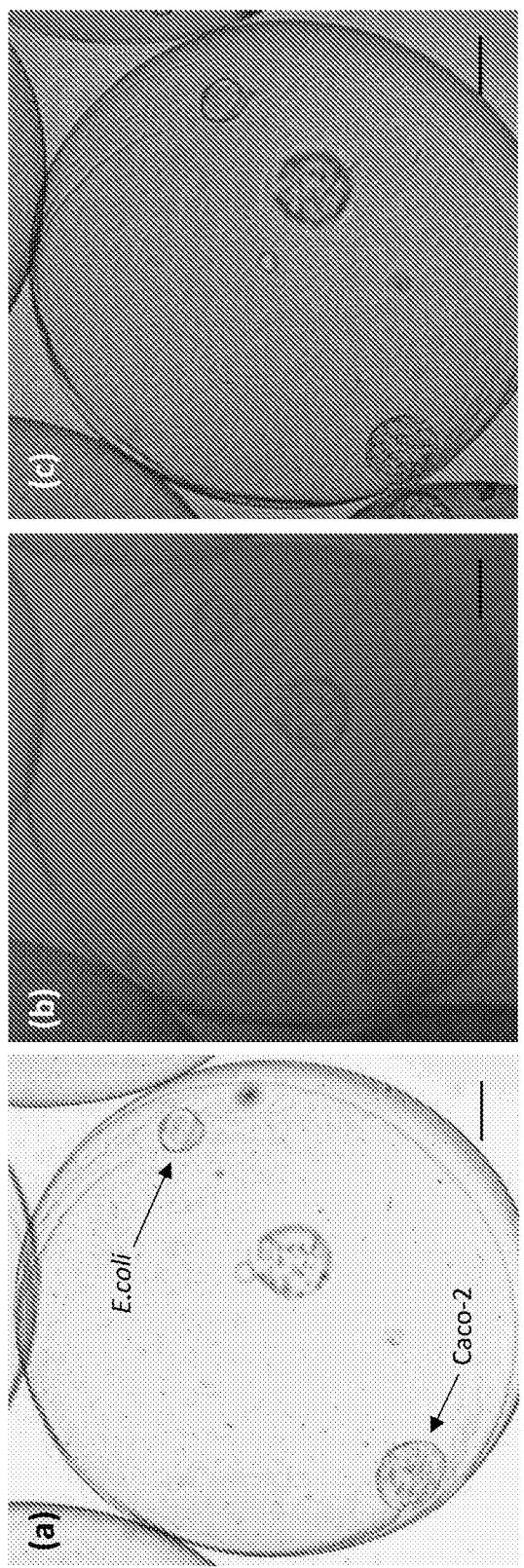
FIG. 12 are brightfield and fluorescence microscopy images immediately after MCC construction. Panel (a) shows a brightfield image of MCC with *E. coli* encapsulated in the smaller inner compartment, and Caco-2 encapsulated in the larger inner compartment. Panel (b) shows a fluorescence image of the MCC with *E. coli* encapsulated in the smaller inner compartment and Caco-2 encapsulated in the larger inner compartment, with red filter (which thus appeared a bright red color). Panel (c) shows a fluorescence image of the MCC with *E.coli* encapsulated in the smaller inner compartment and Caco-2 encapsulated in the larger inner compartment, with green filter (which thus appeared a bright green color). Scale bars in panels (a), (b) and (c) represent 200 µm.
Figure 13:
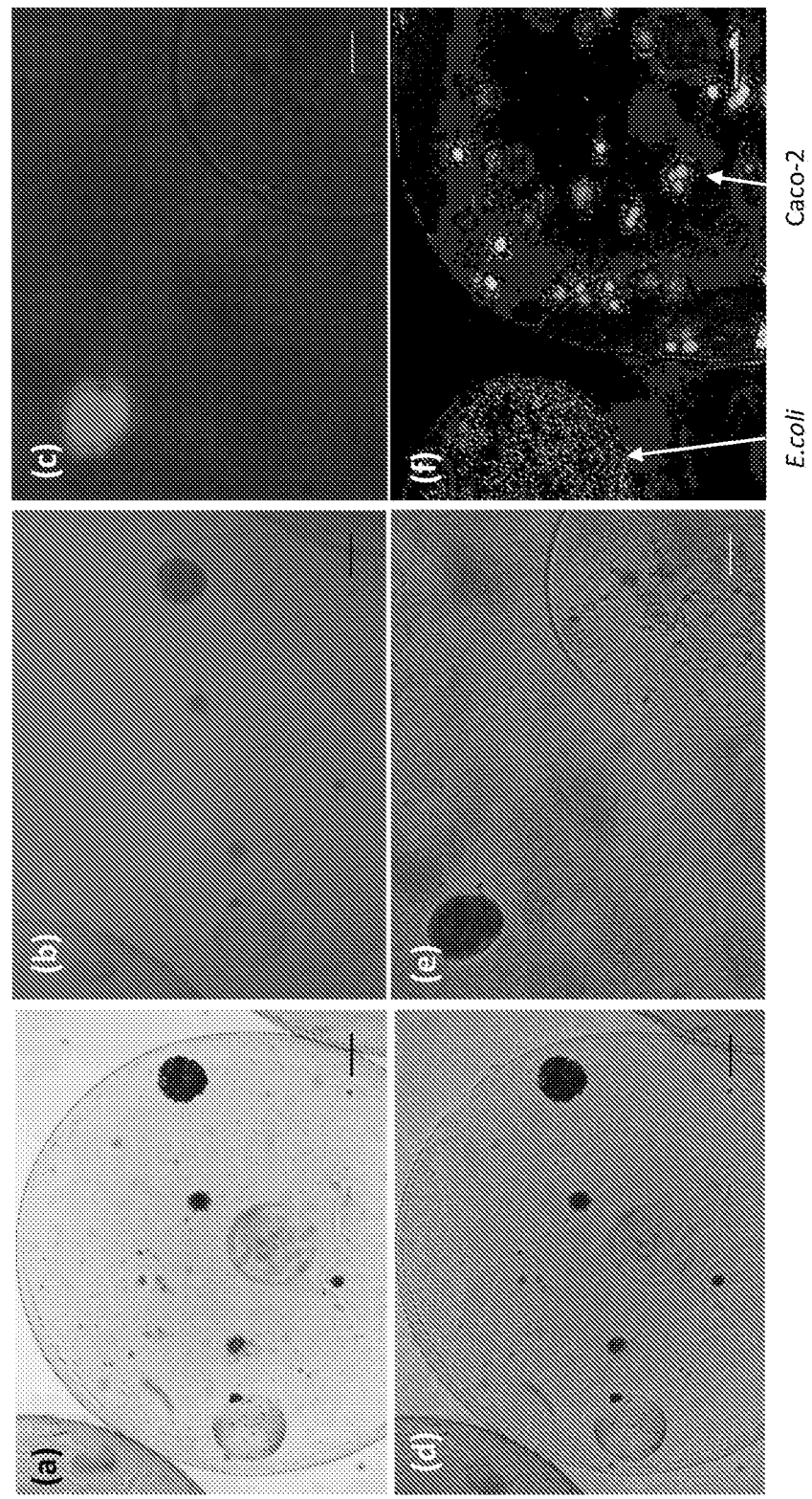
FIG. 13 are brightfield and fluorescent microscope images of the MCCs of FIG. 12 after 18-hour incubation. Panel (a) shows a brightfield image of the MCC with *E. coli* encapsulated in the smaller inner compartment, and Caco-2 encapsulated in the larger inner compartment. Panel (b) shows a fluorescence image of MCC with *E. coli* encapsulated in the smaller inner compartment, and Caco-2 encapsulated in the larger inner compartment, with red filter at 2.5× magnification (which thus appeared a bright red color). Scale bars for panels (a) and (b) represent 100 µm. Panel (c) shows a further magnified fluorescence image of MCC with *E.coli* encapsulated in the smaller inner compartment, and Caco-2 encapsulated in the larger inner compartment, with red filter at 10× magnification. Scale bar for panel (c) represents 50 µm. Panel (d) shows a fluorescence image of MCC with *E.coli* encapsulated in the smaller inner compartment, and Caco-2 encapsulated in the larger inner compartment, with green filter at 2.5× magnification (which thus appeared a bright green color). Scale bar for panel (d) represents 100 µm. Panel (e) shows a further magnified fluorescence image of MCC with *E.coli* encapsulated in the smaller inner compartment, and Caco-2 encapsulated in the larger inner compartment, with green filter at 10× magnification. Scale bar in panel (e) represents 50 µm. Panel (f) shows a confocal image of the inner compartments, with green fluorescence showing Caco-2 (shown in the right of the image), and red fluorescence showing *E.coli* (shown in the left of the image). Scale bar in panel (f) represents 50 µm.

Discussion. Bright field and fluorescent images of MCCs immediately after construction are shown in FIG. 12. Images of the MCCs after 18-hour incubation are shown FIG. 13. No dye was necessary for the bacteria given modified *E. coli* that produced red fluorescence was used for the experiment. In case of Caco-2, Calcein AM, a membrane dye that gives green fluorescence to live mammalian cells, was used for images. Fluorescence from the inner compartments was not overly prominent when observed under fluorescent microscope. However, fluorescence from the cells inside the inner compartments appeared much more clearly when observed under confocal microscope.

All identified publications and references are herein incorporated by reference to the same extent as if each individual publication was specifically and individually indicated to be incorporated by reference in its entirety. While the invention has been described in connection with exemplary embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the features hereinbefore set forth.

What is claimed is:

1. A method of synthesizing a multicompartment capsule, comprising the steps of:
   I. forming at least one plurality of polymer capsules via a capsule-forming process, wherein said capsule-forming process comprises:
      A. providing a feed solution comprising a biopolymer;
      B. providing a reservoir solution comprising a biopolymer, wherein said feed solution biopolymer and said reservoir solution biopolymer have opposite charges; and
      C. introducing droplets of said feed solution into said reservoir solution, thereby forming via electrostatic complexation a plurality of polymer capsules;
   II. encapsulating at least one polymer capsule(s) from said formed plurality of polymer capsules in an outer polymer shell, comprising:
      A. providing a feed solution comprising a biopolymer and at least one polymer capsule(s) from said formed plurality of polymer capsules;
      B. providing a reservoir solution comprising a biopolymer, wherein said feed solution biopolymer and said reservoir solution biopolymer have opposite charges; and
      C. introducing droplets of said feed solution into said reservoir solution, thereby forming via electrostatic complexation a plurality of outer polymer shells, wherein at least one of said outer polymer shells encapsulates said at least one polymer capsule(s), thereby forming a multicompartment capsule, wherein said feed solution of either of steps I (A) or II (A) further comprises a payload, wherein at least one polymer capsule(s) from savid formed polymer capsules encapsulates said payload.

2. The method of claim 1, comprising the step of forming one or more additional plurality of polymer capsules by repeating said capsule-forming process.

3. The method of claim 2, wherein said encapsulating step comprises encapsulating at least one polymer capsule from each formed plurality of polymer capsules in said outer polymer shell.

4. The method of claim 2, wherein said multicompartment capsule encapsulates two or more polymer capsules having different diameters.

5. The method of claim 2, wherein said multicompartment capsule encapsulates two or more polymer capsules having different payloads.

6. The method of claim 1, wherein said feed solution of either of steps I (A) or II (A) comprises one of an anionic biopolymer or a cationic biopolymer, and said reservoir solution of either of steps I (B) or II (B) comprises the other of said anionic biopolymer or said cationic biopolymer.

7. The method of claim 1, wherein said introducing step during said capsule-forming process comprises the further steps of:

(1) channeling said feed solution through a first capillary; and (2) exposing a tip of said first capillary to pulses of gas and thereby dislodging via each pulse of gas a droplet of said feed solution from said tip, said dislodged droplets of said feed solution introduced into said reservoir solution.

8. The method of claim 7, wherein said introducing step during said encapsulating comprises the further steps of:

(1) channeling said feed solution through a second capillary; and (2) exposing a tip of said second capillary to pulses of gas and thereby dislodging via each pulse of gas a droplet of said feed solution from said tip, said dislodged droplets of said feed solution introduced into said reservoir solution.

9. The method of claim 8, wherein said first capillary has a first diameter, and said second capillary has a second diameter greater than said first diameter.

10. The method of claim 1, wherein said multicompartment capsule encapsulates two or more polymer capsules, one of said polymer capsules encapsulating a first payload and another of said polymer capsules encapsulating a second payload.

11. The method of claim 1, wherein said at least one polymer capsule(s) has an outer membrane permeable to ions and small molecules.

* * * * *